(12) United States Patent
Nagata et al.

(10) Patent No.: US 8,455,229 B2
(45) Date of Patent: Jun. 4, 2013

(54) RNA POLYMERASE DERIVED FROM INFLUENZA VIRUS

(75) Inventors: Kyosuke Nagata, Ibaraki (JP); **Atsush

OTHER PUBLICATIONS

Stouffer et al., "Structural basis for the functional and inhibition of an influenza virus proton channel," Nature (Jan. 31, 2008) vol. 451, pp. 596-600.

Tardendeau et al., "Structure and nuclear import function of the C-terminal domain of influenza virus polymerase B2 subunit," Nature Structural & Molecular Biology (Mar. 2007) vol. 14, No. 3, pp. 229-233.

von Itzstein et al., "Rational design of potent sialidase-based inhibitors of influenza virus replication," Nature (Jun. 3, 1993) vol. 363, pp. 418-423.

Wang et al., "Ion channel activity of influenza A virus M2 protein: characterization of the amantadine block," Journal of Virology (Sep. 1993) vol. 67, No. 9, pp. 5585-5594.

Zurcher et al., "Mutational analysis of the influenza virus A/Victoria/3/75 PA protein: studies of interaction with PB1 protein and identification of a dominant negative mutant," Journal of General Virology (1996) vol. 77, pp. 1745-1749.

Area, et al., "3D Structure of the Influenza Virus Polymerase Complex: Localization of Subunit Domains," Proceedings of the National Academy of Sciences of the United States of America, vol. 101, No. 1, p. 308-13, 2004.

De Clercq, et al., "Avian Influenza A (H5N1) Infection: Targets and Strategies for Chemotherapeutic Intervention," Trends in Pharmacological Sciences, vol. 28, No. 6, p. 280-285, 2007.

International Search Report for PCT/JP2009/062140, dated Oct. 6, 2009.

Obayashi, et al., "The Structural Basis for an Essential Subunit Interaction in Influenza Virus RNA Polymerase," Nature, vol. 454, p. 1127-1132, 2008.

Ohtsu, et al., "Fine Mapping of the Subunit Binding Sites of Influenza Virus RNA Polymerase," Microbiology and Immunology, vol. 46, No. 3, p. 167-75, 2002.

Perez, et al., "Functional Analysis of PA Binding by Influenza a Virus PB1: Effects on Polymerase Activity and Viral Infectivity," Journal of Virology, vol. 75, No. 17, p. 8127-8136, 2001.

Torreira, et al., "Three-Dimensional Model for the Isolated Recombinant Influenza Virus Polymerase Heterotrimer," Nucleic Acids Research, vol. 35, No. 11, p. 3774-3783, 2007.

Deng et al., "In Vitro Assembly of PB2 with a PB1-PA Dimer Supports a New Model of Assembly of Influenza A Virus Polymerase...," Journal of Virology (Jul. 2005), vol. 79, No. 13, pp. 8669-8674.

Extended European Search Report issued Oct. 14, 2011, in European Patent Application No. 09773545.0.

Ghanem et al., "Peptide-Mediated Interference with Influenza A Virus Polymerase," Journal of Virology (Jul. 2007), vol. 81, No. 14, pp. 7801-7804.

He et al., "Crystal Structure of the polymerase PAc-PB1N complex from an avian influenza H5N1 virus," Nature (Aug. 2008), vol. 454, pp. 1123-1127.

Toyoda et al., "Molecular assembly of the influenza virus RNA polymerase: determination of the subunit-subunit contact sites," Journal of General Virology (1996), vol. 77, pp. 2149-2157.

Wiencek, J.M., "New Strategies for Protein Crystal Growth", Annu. Rev. Biomed. Eng., (1999), vol. 1, pp. 505-534.

* cited by examiner a  b

RNA POLYMERASE DERIVED FROM INFLUENZA VIRUS

TECHNICAL FIELD

The present invention relates to the construction of an expression system for influenza virus RNA polymerase, crystallization of the influenza virus RNA polymerase, and a method for screening a substance capable of serving as an active ingredient in anti-influenza drugs.

BACKGROUND ART

Influenza virus is an RNA virus having negative-strand RNA as its genome. Frequent mutations occur in the phenotype or genomic nucleotide sequences of influenza virus, and hence the virus occasionally give rises inter-specie infection.

Influenza A virus is a major human and animal pathogen, which periodically causes a global pandemic and may result in a catastrophic loss of life. The recent emergence in Asia of avian influenza related to highly pathogenic forms of the human virus has highlighted the urgent need for new effective treatments (Non-patent Document 1).

Most current influenza drugs target either hemagglutinin (HA) or neuraminidase (NA) on the virus surface. These two major antigens are present on the virion surface (Non-patent Document 2), and 16 different HA subtypes and 9 different NA subtypes have been identified (Non-patent Document 3). Depending on the combination of these subtypes, the type of influenza virus (e.g., H1N1, H3N2, H5N1) is identified. For example, oseltamivir (commercially available under the name "Tamiflu") and zanamivir (Relenza) are NA inhibitors and prevent virus particles being released from infected cells (Non-patent Documents 4 to 7). Oseltamivir is a drug stockpiled with a budget of several billion dollars in response to the new influenza epidemic in Asia. However, oseltamivir-resistant influenza is already emerging, and this drug is of limited use in children due to its side effects. Amantadine, an anti-influenza drug, targets the M2 protein (viral proton channel) (Non-patent Document 8), while another drug has been developed based on the three-dimensional structure of influenza M2 protein (Non-patent Document 9). However, in the case of these drugs targeting the M2 protein, a single residue mutation in M2 is sufficient to confer resistance to the virus, which may render the drugs useless against many strains. Moreover, influenza B virus does not have M2. Both oseltamivir and amantadine target proteins with a single known function and substantial sequence variation between viral strains. Thus, there is a need to develop new lead molecules disrupting other processes in the viral life cycle.

Influenza virus RNA polymerase plays an important role in virus multiplication after infection in humans, and hence can be used as a target for anti-influenza virus agents. However, none of the current medications targets the viral RNA polymerase. The viral RNA polymerase plays an extensive role in viral replication (Non-patent Document 10). This polymerase consists of a heterotrimeric complex with a total molecular weight of approximately 250 kDa, composed of polymerase acidic subunit (PA), polymerase basic subunit 1 (PB1) and polymerase basic subunit 2 (PB2) (Non-patent Document 11). All of these three subunits are required for both transcription and replication (Non-patent Document 12). Until now, very little information has been reported for the structure of the RNA polymerase (Non-patent Documents 13 to 15). In addition, none of the current reports mentions techniques for large-scale expression of the RNA polymerase, which are the key to RNA polymerase studies.

PRIOR ART DOCUMENTS

Non-patent Documents

[Non-patent Document 1] Peiris, J. S. et al., Clin. Microbiol. Rev. 20, 243-267 (2007)
[Non-patent Document 2] Hsieh, H. P. & Hsu, J. T., Curr. Pharm. Des. 13, 3531-42 (2007)
[Non-patent Document 3] World Health Organization., Bull. World Health Organ. 58, 585-591 (1980)
[Non-patent Document 4] Kim, C. U. et al., J. Am. Chem. Soc. 119, 681-690 (1997)
[Non-patent Document 5] von Itzstein, M. et al., Nature 363, 418-423 (1993)
[Non-patent Document 6] Liu, Y., Zhang, J. & Xu, W., Curr. Med. Chem. 14, 2872-91 (2007)
[Non-patent Document 7] Russel, R. J. et al., Nature 443, 45-49 (2006)
[Non-patent Document 8] Wang, C. et al, J. Virol. 67, 5585-5594 (1993); and Stouffer, A. L. et al., Nature 451, 596-599 (2008)
[Non-patent Document 9] Jason R. Schnell and James J. Chou, Nature 451, 591-595 (2008)
[Non-patent Document 10] Braam, J. et al., Cell 34, 609-618 (1983)
[Non-patent Document 11] Horisberger, M. A. Virology 107, 302-305 (1980)
[Non-patent Document 12] Huang, T. S. et al., J. Virol. 64, 5669-5673 (1990)
[Non-patent Document 13] Area, E. et al., Proc. Natl. Acad. Sci. USA 101, 308-313 (2004)
[Non-patent Document 14] Torreira, E. et al., Nucleic Acids Res. 35, 3774-3783 (2007)
[Non-patent Document 15] Tarendeau, F. et al., Nature Struct. Mol. Biol. 14, 299-233 (2007)

DISCLOSURE OF THE INVENTION

Problem to be Solved by the Invention

Under these circumstances, the present invention aims to express influenza virus RNA polymerase on a large scale. The present invention also aims to crystallize the influenza virus RNA polymerase. The present invention further aims to develop an anti-influenza drug targeting the RNA polymerase, which is a protein highly conserved among influenza virus species.

Means to Solve the Problem

As a result of extensive and intensive efforts made to solve the above problems, the inventors of the present invention have used a gene derived from influenza virus to construct an expression system (in *E. coli*) for a complex of RNA polymerase PA and PB1 subunits and establish a method for its crystallization.

Moreover, as a result of structural analysis on the PA-PB1 complex, the inventors of the present invention have succeeded in determining the structure of an interaction site between polymerase acidic subunit (PA) and polymerase basic subunit 1 (PB1), each constituting the RNA polymerase. Then, the inventors have discovered that an amino acid sequence related to this site is highly conserved among virus species, and that the above interaction site is useful as a target site for anti-influenza drugs. These findings led to the completion of the present invention.

Namely, the present invention is as follows.

(1) A complex comprising a polypeptide shown in (a1), (a2) or (a3) below and a polypeptide shown in (b1), (b2) or (b3) below:

(a1) a polypeptide which consists of the amino acid sequence shown in SEQ ID NO: 6;

(a2) a polypeptide which consists of an amino acid sequence with deletion, substitution or addition of one or several amino acids in the amino acid sequence shown in SEQ ID NO: 6 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 5 and which has the same biological activity as the polypeptide shown in (a1); and (b1) a polypeptide which consists of the amino acid sequence shown in SEQ ID NO: 8;

(b2) a polypeptide which consists of an amino acid sequence with deletion, substitution or addition of one or several amino acids in the amino acid sequence shown in SEQ ID NO: 8 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 7 and which has the same biological activity as the polypeptide shown in (b1).

(2) A recombinant vector comprising DNA encoding the polypeptide shown in (a1), (a2) or (a3) and DNA encoding the polypeptide shown in (b1), (b2) or (b3).

(3) A transformed cell carrying DNA encoding the polypeptide shown in (a1), (a2) or (a3) and DNA encoding the polypeptide shown in (b1), (b2) or (b3).

(4) A method for producing the complex according to (1) above, which comprises culturing a transformed cell carrying DNA encoding the polypeptide shown in (a1), (a2) or (a3) and DNA encoding the polypeptide shown in (b1), (b2) or (b3), and collecting the complex according to (1) above from the cultured product.

(5) A crystal of the complex according to (1) above.

(6) The crystal according to (5) above, having a space group of $P3_221$.

(7) The crystal according to (6) above, having an unit lattice of a=b=101.957±50.0 Å and c=115.023±50.0 Å.

(8) A method for producing a crystal of the complex according to (1) above, which comprises crystallizing the complex according to (1) above in the presence of a precipitant.

(9) The method according to (8) above, wherein the precipitant is sodium formate.

(10) A polypeptide shown in (a1), (a2) or (a3) below:

(a1) a polypeptide which consists of the amino acid sequence shown in SEQ ID NO: 6;

(a2) a polypeptide which consists of an amino acid sequence with deletion, substitution or addition of one or several amino acids in the amino acid sequence shown in SEQ ID NO: 6 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 5 and which has the same biological activity as the polypeptide shown in (a1).

(11) DNA encoding the polypeptide according to (10) above.

(12) A recombinant vector comprising the DNA according to (11) above.

(13) A transformed cell carrying DNA encoding the polypeptide according to (10) above.

(14) A method for producing the polypeptide according to (10) above, which comprises culturing a transformed cell carrying DNA encoding the polypeptide according to (10) above, and collecting the polypeptide according to (10) above from the cultured product.

(15) A polypeptide shown in (b1), (b2) or (b3) below:

(b1) a polypeptide which consists of the amino acid sequence shown in SEQ ID NO: 8;

(b2) a polypeptide which consists of an amino acid sequence with deletion, substitution or addition of one or several amino acids in the amino acid sequence shown in SEQ ID NO: 8 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 7 and which has the same biological activity as the polypeptide shown in (b1).

(16) DNA encoding the polypeptide according to (15) above.

(17) A recombinant vector comprising the DNA according to (15) above.

(18) A transformed cell carrying DNA encoding the polypeptide according to (15) above.

(19) A method for producing the polypeptide according to (15) above, which comprises culturing a transformed cell carrying DNA encoding the polypeptide according to (15) above, and collecting the polypeptide according to (15) above from the cultured product.

(20) A method for screening a substance capable of serving as an active ingredient in anti-influenza drugs, which comprises the steps of: allowing acidic subunit or a partial fragment thereof and basic subunit or a partial fragment thereof, each of which constitutes influenza virus RNA polymerase, to contact with each other in the presence of a candidate substance; and selecting a substance which inhibits the interaction between the acidic subunit or partial fragment thereof and the basic subunit or partial fragment thereof.

(21) The method according to (20) above, wherein the acidic subunit consists of a polypeptide shown in (a) or (b) below:

(a) a polypeptide which consists of the amino acid sequence shown in SEQ ID NO: 2; or (b) a polypeptide which consists of an amino acid sequence with deletion, substitution or addition of one or several amino acids in the amino acid sequence shown in SEQ ID NO: 2 and which has the activity of influenza virus RNA polymerase acidic subunit.

(22) The method according to (20) above, wherein the partial fragment of acidic subunit consists of a polypeptide shown in (a) or (b) below:

(a) a polypeptide which consists of an amino acid sequence within 130 residues from the C-terminal end of the amino acid sequence shown in SEQ ID NO: 2; or (b) a polypeptide which consists of an amino acid sequence with deletion, substitution or addition of one or several amino acids in an amino acid sequence within 130 residues from the C-terminal end of the amino acid sequence shown in SEQ ID NO: 2 and which has the activity of influenza virus RNA polymerase acidic subunit.

(23) The method according to (20) above, wherein the basic subunit consists of a polypeptide shown in (a) or (b) below:

(a) a polypeptide which consists of the amino acid sequence shown in SEQ ID NO: 4; or (b) a polypeptide which consists of an amino acid sequence with deletion, substitution or addition of one or several amino acids in the amino acid sequence shown in SEQ ID NO: 4 and which has the activity of influenza virus RNA polymerase basic subunit.

(24) The method according to (20) above, wherein the partial fragment of basic subunit consists of a polypeptide shown in (a) or (b) below:

(a) a polypeptide which consists of an amino acid sequence within 15 residues from the N-terminal end of the amino acid sequence shown in SEQ ID NO: 4; or (b) a polypeptide which consists of an amino acid sequence with deletion, substitution or addition of one or several amino acids in an amino acid sequence within 15 residues from the N-terminal end of the amino acid sequence shown in SEQ ID NO: 4 and which has the activity of influenza virus RNA polymerase basic subunit.

(25) The method according to any one of (20) to (24) above, wherein amino acid residues in the interaction site of acidic subunit comprise at least one amino acid residue selected from the group consisting of Gln 408, Phe 411, Asn 412, Met 595, Glu 617, Thr 618, Trp 619, Pro 620, Ile 621, Glu 623, Val 636, Leu 640, Leu 666, Leu 667, Gln 670, Arg 673, Trp 706 and Phe 710 in the amino acid sequence shown in SEQ ID NO: 2.

(26) The method according to any one of (20) to (24) above, wherein amino acid residues in the interaction site of basic subunit comprise at least one amino acid residue selected from the group consisting of Met 1, Asp 2, Val 3, Asn 4, Pro 5, Thr 6, Leu 7, Leu 8, Phe 9, Leu 10, Lys 11, Val 12, Pro 13 and Ala 14 in the amino acid sequence shown in SEQ ID NO: 4.

(27) The method according to (25) above, wherein amino acid residues in the interaction site of acidic subunit comprise at least one amino acid residue selected from the group consisting of Val 636, Leu 640, Leu 666 and Trp 706 in the amino acid sequence shown in SEQ ID NO: 2.

(28) The method according to (26) above, wherein amino acid residues in the interaction site of basic subunit comprise at least one amino acid residue selected from the group consisting of Asn 4, Pro 5, Thr 6, Leu 7, Leu 8, Phe 9 and Leu 10 in the amino acid sequence shown in SEQ ID NO: 4.

(29) The method according to (26) above, wherein amino acid residues in the interaction site of basic subunit are amino acid residues 5-10 of the amino acid sequence shown in SEQ ID NO: 4.

(30) The method according to any one of (20) to (29) above, wherein the candidate substance is at least one selected from the group consisting of a compound and a salt thereof, a peptide, an antibody, and a nucleic acid.

Effect of the Invention

The present invention enables the large-scale expression of an RNA polymerase PA-PB1 complex. The present invention also enables the provision of a crystal of the RNA polymerase PA-PB1 complex for use in analysis of protein three-dimensional structure. The present invention further provides a method for screening a substance capable of serving as an active ingredient in anti-influenza drugs. Since the interaction site between PA and PB1 locates in a region where amino acid sequence is highly conserved, this site can be used as a target for development of anti-influenza drugs, regardless of the phenotypes of influenza viruses or mutations in their genome.

BRIEF DESCRIPTION OF THE DRAWINGS

FIG. 1 is a ribbon diagram showing the overall structure of PA-PB1 complex. FIG. 1*a* is a ribbon diagram showing the overall folding of PA, with helixes (red), strands (yellow), and coil (green). Helixes are numbered from the N-terminal end. PB1 residues are colored dark blue. The principal β-sheet is formed largely from residues 478-571. FIG. 1*b* is an orthogonal view down the "clamp" formed from helixes 10, 11 and 13. Secondary structure elements of the PA-PB1 complex are shown in the upper side, and the sequence is shown along with the sequence of avian influenza virus (H5N1). Disordered regions are indicated with black broken lines. Amino acid residues are highlighted with different color codes corresponding to their conservation levels. Hydrogen bonds between PA and PB1, red; hydrophobic contacts between PA and PB1, dark blue.

FIG. 2 shows an amino acid sequence alignment of human influenza (H1N1) PA (SEQ ID NO: 6) and PB1 (SEQ ID NO: 8) with avian influenza (H5N1) PA (SEQ ID NO: 10) and PB1 (SEQ ID NO: 12).

FIG. 3 is a schematic diagram showing hydrogen bonds between PA and PB1. Dashed lines (blue) indicate hydrogen bonds of 2.4 to 3.5 Å in length.

FIG. 4 is a molecular surface representation showing the cleft into which PB1 binds.

FIG. 5 shows the van der Waals surface of the interface domain in protein representation, rotated by 180° around the horizontal axis relative to the van der Waals surface in FIG. 4(*a*). The salt bridge formed between Glu 623 and His 713 holds the β-hairpin of PA (residues Ile 621 to Glu 630) over the PB1 peptide.

FIG. 6 shows the electrostatic potential of PA and PB1. FIG. 6*a* shows the protein's van der Waals surface colored according to the electrostatic potential of PA. Red indicates negative charge, and blue indicates positive charge. The cut-off level ranges from −15 to +15 KBT-1. The PA molecule is in the same orientation as shown in FIG. 1*b*. FIG. 6*b* shows the protein's van der Waals surface colored according to the electrostatic potential of PB1.

FIG. 7 shows hydrophobic contacts between PA and PB1.

FIG. 8 shows electron density maps of the PA-PB1 complex. a): Electron density map covering major PB1 residues in the complex (2mFo-DFc). The map was calculated from reflections with amplitudes in the resolution range of 50.0 to 2.3 Å, and contoured at 1.2σ (σ is the standard deviation of the electron density map). There is no contact between Thr 6 of PB1 and PA, suggesting that substitution at this site may make use of interactions with the exposed side chains of Leu 666 and Phe 707. The PA and PB1 subunits are shown in a stick model (PA: black label, carbon atoms are shown in yellow, nitrogen atoms in light blue, and oxygen atoms in red; PB1: red label and stick model). b): Electron density map covering major PB1 residues in the complex (2mFo-DFc). The map was calculated from reflections with amplitudes in the resolution range of 50.0 to 2.3 Å, and contoured at 1.2σ (σ is the standard deviation of the electron density map). The salt bridge formed between Glu 623 and His 713 holds the β-hairpin of PA (residues Ile 621 to Glu 630) over the PB1 peptide. Black dashed lines indicate hydrogen bonds (3.2 Å).

FIG. 9 shows the structure of PA-PB1 co-expression system (pET28HisTEV-PA(239-716)-PB1(1-81)). cDNAs encoding amino acid positions 239-716 of the PA subunit and amino acid positions 1-81 of the PB1 subunit obtained from A/Puerto Rico/8/1934 are tandemly integrated into pET28b. Although both subunits are controlled by a single T7 promoter, an SD sequence serving as a ribosomal binding site is located upstream of each subunit-encoding DNA, which allows co-expression of two peptide chains from a single RNA molecule. A histidine tag and a TEV protease recognition site are integrated between restriction sites NdeI and BamHI to thereby express histidine-tagged residues 239-716 of the PA subunit. Residues 1-81 of the PB1 subunit have no histidine tag, but can be co-purified by being bound directly to residues 239-716 of the PA subunit.

FIG. 10 shows the binding activity between PA various mutants and PB1, as well as the transcription activity of the complex. FIG. 10a shows the details of interaction between PA and PB1. PA and PB1 residues are shown in green and yellow, respectively. Mutated sites are shown in blue. FIG. 10b shows the results of GST pull-down assay. PA variants (upper: half volume for pull-down assay) were pulled down with GST-fused N-terminal 14 residues of PB1 (middle) or GST as a negative control (bottom) and analyzed by 5-20% SDS-PAGE and Coomassie staining. The PA variants used are as follows: Lane 1: WT; Lane 2: C-terminal end (239-657) with deletion of 657; Lane 3: deletion of 619-630; Lane 4: V636S; Lane 5: L640D; Lane 6: L666D; Lane 7: W706A; Lane 8: F710A. FIG. 10c represents effects of various mutations of PA on the level of viral RNAs synthesis in reporter assays.

BEST MODES FOR CARRYING OUT THE INVENTION

Figure 1:
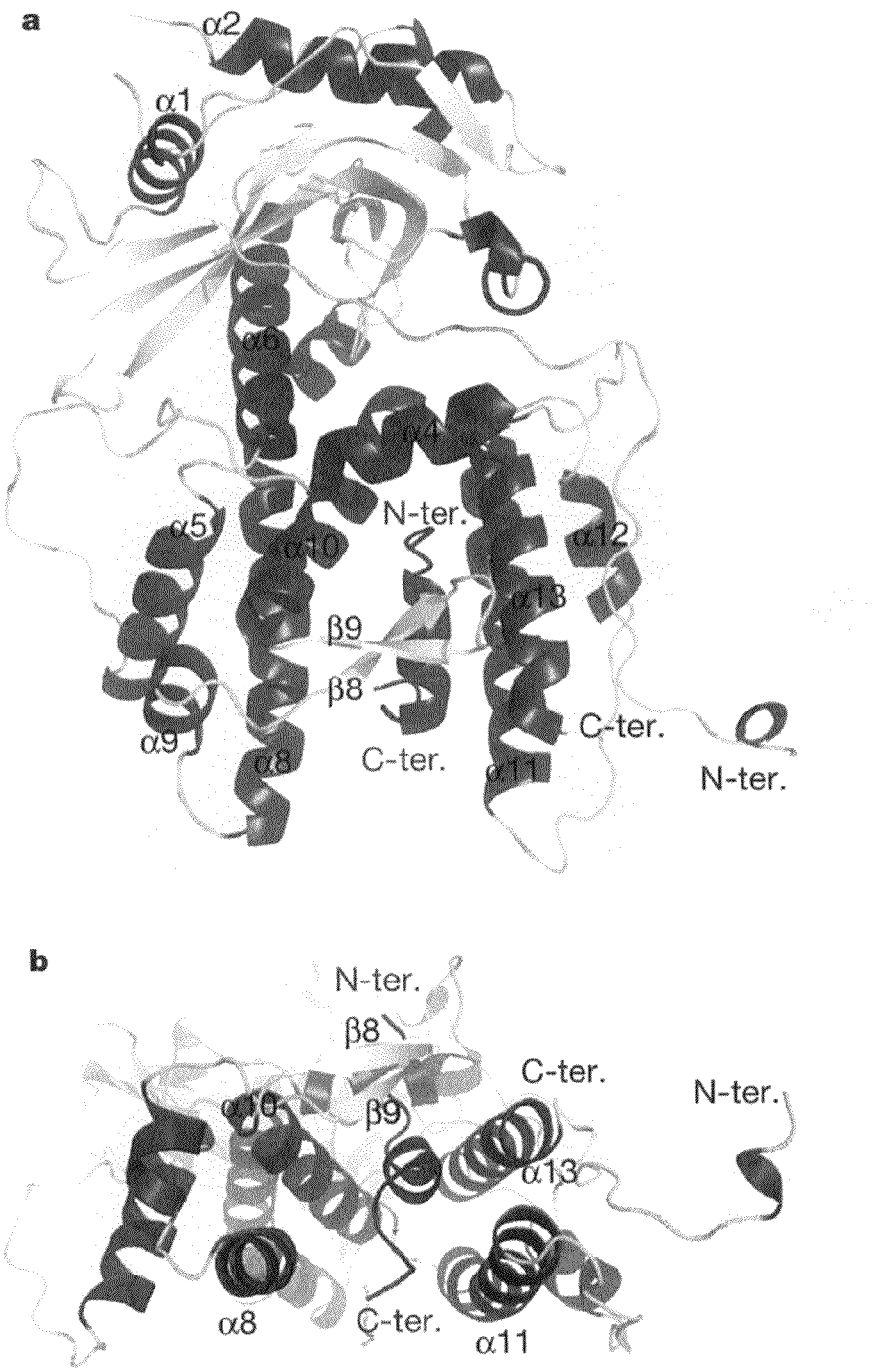

The present invention will be described in more detail below. The following embodiments are illustrated to describe the present invention, and it is not intended to limit the present invention thereto. The present invention can be implemented in various modes, without departing from the spirit of the present invention.

It should be noted that all documents cited herein, including prior art documents, patent gazettes and other patent documents, are incorporated herein by reference. Moreover, this specification incorporates the contents disclosed in the specifications of the Japanese patent applications filed on Jul. 2, 2008 and Jan. 27, 2009 (Japanese Patent Application Nos. 2008-173567 and 2009-015497), based on which the present application claims priority.

In the present invention, RNA polymerase and each subunit thereof are as described below.

1. RNA Polymerase (1) RNA-Dependent RNA Polymerase Complex

The RNA-dependent RNA polymerase complex of influenza virus is a protein complex associating with the 5'- and 3'-termini of influenza virus genome and is essential for viral transcription and replication.

This complex also plays an essential role in developing viral pathogenicity. For example, by cap snatching, the complex recognizes the cap structure of host mRNA and cleaves the host mRNA including the cap structure.

The RNA polymerase complex is composed of three subunits, i.e., PA, PB1 and PB2. All of these three subunits are required for viral transcription and replication.

Although some reports have been issued for the structure of these subunits, their structural information is very limited (Area, E. et al., Proc. Natl. Acad. Sci. USA 101, 308-313 (2004); Torreira, E. et al. Nucleic Acids Res. 35, 3774-3783 (2007); Tarendeau, F. et al. Nature Struct. Mol. Biol. 14, 229-233 (2007); Guilligay, D. et al. Nature Struct. Mol. Biol. 15, 500-506 (2008)). This means that the X-ray crystal structure analysis of the influenza virus RNA polymerase complex as such was very difficult for those skilled in the art.

(2) Polymerase Acidic Subunit (PA)

PA is involved in assembly of the functional complex. The carboxy-terminal domain of PA forms a highly hydrophobic groove with which PB1 interacts.

Examples of PA used in the present invention include a polypeptide which consists of the amino acid sequence shown in SEQ ID NO: 2.

In addition to such a polypeptide which consists of the amino acid sequence shown in SEQ ID NO: 2, some variants of this polypeptide also have interactions with PB1. Thus, in the present invention, it is also possible to use a polypeptide which consists of an amino acid sequence with deletion, substitution or addition of one or several amino acids in the amino acid sequence shown in SEQ ID NO: 2 and which has the activity of influenza virus RNA polymerase acidic subunit.

Moreover, a partial fragment of PA may also be used for this purpose. To form a conformation required for PA to interact with PB1, it would be sufficient to contain a region specific for this purpose, which is composed of C-terminal 130 amino acids in the amino acid sequence of PA. Thus, such a partial fragment includes the following polypeptides:

(a) an amino acid sequence which corresponds to amino acids 239-716 of SEQ ID NO: 2 (SEQ ID NO: 6);

(b) an amino acid sequence which consists of an amino acid sequence with deletion, substitution or addition of one or several amino acids in the amino acid sequence shown in SEQ ID NO: 6 and which has the same biological activity as the polypeptide of SEQ ID NO: 6;

(c) a polypeptide which is encoded by DNA hybridizable under stringent conditions with DNA complementary to DNA consisting of the nucleotide sequence shown in SEQ ID NO: 5 and which has the same biological activity as the polypeptide of SEQ ID NO: 6;

(d) a polypeptide which consists of an amino acid sequence within 130 residues from the C-terminal end of the amino acid sequence shown in SEQ ID NO: 2; and (e) a polypeptide which consists of an amino acid sequence with deletion, substitution or addition of one or several amino acids in an amino acid sequence within 130 residues from the C-terminal end of the amino acid sequence shown in SEQ ID NO: 2 and which has the activity of influenza virus RNA polymerase acidic subunit.

The term "PA" or "acidic subunit" is used herein to encompass either or both the full-length polypeptide of influenza virus RNA polymerase acidic subunit and a partial fragment thereof.

In the context of the present invention, "the same biological activity as a polypeptide which consists of the amino acid sequence shown in SEQ ID NO: 6" is intended to encompass the activity of RNA polymerase acidic subunit, as well as activity as an antigen, activity as an immunogen and so on. The "activity of RNA polymerase acidic subunit" is intended to mean binding activity with β-subunit. RNA polymerase activity acquired by binding of PA to a PB1-PB2 complex, and complex formation activity acquired by binding of PA to PB1 are both encompassed by the "activity of RNA polymerase acidic subunit" defined above. Moreover, the "activity of RNA polymerase acidic subunit" in variants is intended to mean having at least 30% or more, preferably 50% or more, more preferably 90% or more activity, as compared to the activity of PA consisting of the amino acid sequence shown in SEQ ID NO: 2. Thus, the above PA fragments (b), (c) and (e) have at least 30% or more, preferably 50% or more, more preferably 90% or more PA activity, as compared to the activity of PA consisting of the amino acid sequence shown in SEQ ID NO: 2.

In the present invention, a polynucleotide encoding PA can be obtained, for example, by gene amplification (polymerase chain reaction: PCR) in which primers are designed based on the nucleotide sequence shown in SEQ ID NO: 1 or a partial sequence thereof, and influenza virus genomic cDNA is used as a template (Current Protocols in Molecular Biology, John Wiley & Sons (1987) Section 6.1-6.4).

In the present invention, nucleotide sequences can be confirmed by sequencing in a conventional manner. For example, dideoxynucleotide chain termination (Sanger et al. (1977) Proc. Natl. Acad. Sci. USA 74: 5463) or other techniques can be used for this purpose. Moreover, an appropriate DNA sequencer can also be used to analyze the sequences.

A polynucleotide encoding PA can be obtained by reverse transcription reaction and PCR reaction, in which primers are designed to give a desired sequence, based on sequence information of the full-length nucleotide sequence or amino acid sequence shown in SEQ ID NO: 1 or 2 or a partial sequence thereof, and the viral genome purified from influenza virus particles is used as a template. For reverse transcription reaction, reference may be made to "Molecular Cloning, A Laboratory Manual 2nd ed." (Cold Spring Harbor Press (1989)). Moreover, these primers can be used to obtain a desired fragment by PCR amplification from a polynucleotide containing a PA-encoding gene. In this case, the primers may be modified to have an appropriate restriction enzyme sequence(s) or the like in order to facilitate cloning of the amplification product into a vector.

A polynucleotide encoding a mutated amino acid sequence with deletion, substitution or addition of one or several amino acids in the amino acid sequence shown in SEQ ID NO: 2 or 6 can be prepared according to site-directed mutagenesis or other techniques, as described in "Molecular Cloning, A Laboratory Manual 2nd ed." (Cold Spring Harbor Press (1989)), "Current Protocols in Molecular Biology" (John Wiley & Sons (1987-1997)), Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6, etc.

To introduce mutations into the polynucleotides for preparation of the above PA variants, it is also possible to use a mutation introduction kit based on site-directed mutagenesis (e.g., Kunkel method, Gapped duplex method), such as a QuikChange™ Site-Directed Mutagenesis Kit (Stratagene), a GeneTailor™ Site-Directed Mutagenesis System (Invitrogen), a TaKaRa Site-Directed Mutagenesis System (e.g., Mutan-K, Mutan-Super Express Km; Takara Bio Inc., Japan).

"Stringent conditions" may be selected as appropriate by those skilled in the art. Hybridization conditions may be low stringent conditions, by way of example. Low stringent conditions include, for example, "2×SSC, 0.1% SDS, 42° C." or "1×SSC, 0.1% SDS, 37° C." More stringent conditions include, for example, conditions of "1×SSC, 0.1% SDS, 65° C.", "0.5×SSC, 0.1% SDS, 50° C." or "2×SSC, 0.1% SDS, 50° C." More preferably, high stringent conditions include, for example, "2×SSC, 0.1% SDS, 65° C." Under these conditions, when the temperature of hybridization reaction is lowered, not only DNAs with high homology, but also DNAs with only low homology can be obtained comprehensively. Conversely, it can be expected that only DNAs with high homology are obtained at an elevated hybridization temperature. However, not only the temperature but also a plurality of factors (e.g., salt concentration) will affect the stringency of hybridization, and those skilled in the art would achieve the desired stringency by selecting these factors as appropriate. Hybridization may be accomplished in a known manner. For detailed procedures of hybridization, reference may be made to, for example, "Molecular Cloning, A Laboratory Manual 2nd ed." (Cold Spring Harbor Laboratory Press (1989)), "Current Protocols in Molecular Biology" (John Wiley & Sons (1987-1997)), etc.

In the context of the present invention, PA further encompasses a fusion protein having another peptide sequence added thereto. As a peptide sequence added to PA, a tag sequence that facilitates protein detection may be selected, including hemagglutinin (HA), glutathione S transferase (GST), hexahistidine tag (e.g., 6×His, 10×His), maltose-binding protein (MBP), green fluorescent protein (GFP), red fluorescent protein (DsRed), Luciferase or Venus. Such a tag sequence may be easily linked to PA through standard genetic engineering procedures. Alternatively, it is also possible to use a commercially available vector. Examples of such a vector include pGEX series (Amersham Pharmacia Biotech), pET Expression System (Novagen) and so on.

(2) Basic Subunit 1

Basic subunit 1 (PB1) has a polymerase active site. Amino-terminal residues of PB1 form a $3_{10}$ helix. This structure fits into the above highly hydrophobic groove in PA.

Examples of PB1 in the present invention include a polypeptide which consists of the amino acid sequence shown in SEQ ID NO: 4.

In addition to such a polypeptide which consists of the amino acid sequence shown in SEQ ID NO: 4, some variants of this polypeptide also have interactions with PA. Thus, in the method of the present invention, it is also possible to use a polypeptide which consists of an amino acid sequence with deletion, substitution or addition of one or several amino acids in the amino acid sequence shown in SEQ ID NO: 4 and which has the activity of influenza virus RNA polymerase basic subunit.

A partial fragment of PB1 may also be used in the present invention. To form a conformation required for PB1 to interact with PA, it would be sufficient to contain a sequence of N-terminal 15 amino acids in the amino acid sequence of PB1. Thus, such a partial fragment includes the following polypeptides:

(a) an amino acid sequence which corresponds to amino acids 1-81 of SEQ ID NO: 4 (SEQ ID NO: 8);

(b) an amino acid sequence which consists of an amino acid sequence with deletion, substitution or addition of one or several amino acids in the amino acid sequence shown in SEQ ID NO: 8 and which has the same biological activity as the polypeptide of SEQ ID NO: 8;

(c) a polypeptide which is encoded by DNA hybridizable under stringent conditions with DNA complementary to DNA consisting of the nucleotide sequence shown in SEQ ID NO: 7;

(d) a polypeptide which consists of an amino acid sequence within 15 residues from the N-terminal end of the amino acid sequence shown in SEQ ID NO: 4; and (e) a polypeptide which consists of an amino acid sequence with deletion, substitution or addition of one or several amino acids in an amino acid sequence within 15 residues from the N-terminal end of the amino acid sequence shown in SEQ ID NO: 4 and which has the activity of influenza virus RNA polymerase basic subunit.

The term "PB1" or "basic subunit" is used herein to encompass either or both the full-length polypeptide of influenza virus RNA polymerase basic subunit and a partial fragment thereof.

In the context of the present invention, "the same biological activity as the polypeptide of SEQ ID NO: 8" is intended to encompass the activity of RNA polymerase basic subunit, as well as activity as an antigen, activity as an immunogen and so on. The "activity of RNA polymerase basic subunit" is intended to mean binding activity with PA. RNA polymerase activity acquired by binding of PB1 to PA and PB2 to form a complex, and complex formation activity acquired by binding of PB1 to PA are both encompassed by the "activity of RNA polymerase basic subunit" defined above. Moreover, the "activity of RNA polymerase basic subunit" in variants is intended to mean having at least 30% or more, preferably 50% or more, more preferably 90% or more activity, as compared to the activity of PB1 consisting of the amino acid sequence shown in SEQ ID NO: 4. Thus, the above PB1 fragments (b), (c) and (e) have at least 30% or more, preferably 50% or more, more preferably 90% or more PB1 activity, as compared to the activity of PB1 consisting of the amino acid sequence shown in SEQ ID NO: 4.

With respect to other information about PB1, including procedures for site-directed mutagenesis, addition of a tag sequence, definition of stringent conditions, procedures for hybridization, embodiments of mutations, and conditions for PCR reaction, they are the same as those described above, except that the intended nucleotide sequence and amino acid sequence are SEQ ID NO: 3 and SEQ ID NO: 4, respectively.

2. Embodiments of the Present Invention (1) RNA Polymerase Complex

As a first embodiment, the present invention provides a complex comprising a polypeptide shown in (a1), (a2) or (a3) below and a polypeptide shown in (b1), (b2) or (b3) below:

(a1) a polypeptide which consists of the amino acid sequence shown in SEQ ID NO: 6;

(a2) a polypeptide which consists of an amino acid sequence with deletion, substitution or addition of one or several amino acids in the amino acid sequence shown in SEQ ID NO: 6 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 5 and which has the same biological activity as the polypeptide shown in (a1); and (b1) a polypeptide which consists of the amino acid sequence shown in SEQ ID NO: 6;

(b2) a polypeptide which consists of an amino acid sequence with deletion, substitution or addition of one or several amino acids in the amino acid sequence shown in SEQ ID NO: 6 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 5 and which has the same biological activity as the polypeptide shown in (b1).

The polypeptide shown in (a1), (a2) or (a3) is able to bind to and form a complex with the polypeptide shown in (b1), (b2) or (b3).

In this embodiment, there is no particular limitation on the total number and position of amino acids to be deleted, substituted or added. The total number of amino acids to be deleted, substituted or added is one or more, preferably one or several. More specifically, it generally ranges from 1 to 10, preferably from 1 to 5, and more preferably from 1 to 2 for deletion, generally from 1 to 20, preferably from 1 to 10, and more preferably from 1 to 3 for substitution, or generally from 1 to 10, preferably from 1 to 5, and more preferably from 1 to 2 for addition.

The polypeptide shown in (a2) may be exemplified by a polypeptide which consists of the amino acid sequence shown in SEQ ID NO: 10. The amino acid sequence shown in SEQ ID NO: 10 is an amino acid sequence corresponding to amino acids 239-716 of the RNA polymerase PA subunit in influenza A virus (A/Duck/Hong Kong/2986.1/2000 (H5N1)).

The polypeptide shown in (b2) may be exemplified by a polypeptide which consists of the amino acid sequence shown in SEQ ID NO: 12. The amino acid sequence shown in SEQ ID NO: 12 is an amino acid sequence at positions 1-81 of the RNA polymerase PB1 subunit in influenza A virus (A/Duck/Hong Kong/2986.1/2000 (H5N1)).

Moreover, the polypeptides shown in (a3) and (b3) usually share an amino acid sequence homology of 97% or more, preferably 98% or more, more preferably 99% or more with the polypeptides shown in (a1) and (b1), respectively. The homology of each polypeptide can be determined by using software based on the algorithm described in Wilbur, W. J. and Lipman, D. J. Proc. Natl. Acad. Sci. USA (1983) 80, 726-730 or by using known software such as BLAST.

The complex of the present invention can be produced by culturing a transformed cell carrying DNA encoding the polypeptide shown in (a1), (a2) or (a3) and DNA encoding the polypeptide shown in (b1), (b2) or (b3), and collecting the desired complex from the cultured product.

Such a transformed cell carrying DNA encoding the polypeptide shown in (a1), (a2) or (a3) and DNA encoding the polypeptide shown in (b1), (b2) or (b3) may be obtained by transfecting an appropriate host cell with a recombinant vector comprising DNA encoding the polypeptide shown in (a1), (a2) or (a3) and DNA encoding the polypeptide shown in (b1), (b2) or (b3). The present invention also provides such a transformed cell carrying DNA encoding the polypeptide shown in (a1), (a2) or (a3) and DNA encoding the polypeptide shown in (b1), (b2) or (b3).

To construct such a recombinant vector, a DNA fragment covering the coding region of a desired polypeptide may be prepared in an appropriate length, as described above. In the nucleotide sequence of the coding region of the desired polypeptide, one or more nucleotides may be substituted to give a codon(s) optimal for expression in host cells.

Then, this DNA fragment may be inserted downstream of a promoter in an appropriate expression vector to construct a recombinant vector (see, e.g., Molecular Cloning 2nd Edition, J. Sambrook et al., Cold Spring Harbor Lab. Press, 1989). A DNA fragment should be integrated into an expression vector such that the fragment exerts its functions. For this purpose, the intended DNA fragment is inserted into an expression vector such that the codon thereof is in frame with a sequence of desired amino acids. The present invention also provides such a recombinant vector comprising DNA encoding the polypeptide shown in (a1), (a2) or (a3) and DNA encoding the polypeptide shown in (b1), (b2) or (b3).

DNA encoding the polypeptide shown in (a1), (a2) or (a3) and DNA encoding the polypeptide shown in (b1), (b2) or (b3) can be prepared as described above by PCR amplification using influenza virus cDNA as a template.

Such DNA encoding the polypeptide shown in (a1), (a2) or (a3) may be exemplified by DNA consisting of the nucleotide sequence shown in SEQ ID NO: 5, and DNA hybridizable under stringent conditions with DNA complementary to DNA consisting of the nucleotide sequence shown in SEQ ID NO: 5, etc. Such DNA hybridizable under stringent conditions with DNA complementary to DNA consisting of the nucleotide sequence shown in SEQ ID NO: 5 may be exemplified by DNA sharing a homology of at least 88% or more, preferably 90% or more, more preferably 95% or more with the DNA consisting of the nucleotide sequence shown in SEQ ID NO: 5. Such DNA hybridizable under stringent conditions with DNA complementary to DNA consisting of the nucleotide sequence shown in SEQ ID NO: 5 may also be exemplified by DNA consisting of the nucleotide sequence shown in SEQ ID NO: 9. The nucleotide sequence shown in SEQ ID NO: 9 is the nucleotide sequence of DNA encoding an amino acid sequence at positions 239-716 of the RNA polymerase PA subunit in influenza A virus (A/Duck/Hong Kong/2986.1/2000 (H5N1)).

DNA encoding the polypeptide shown in (b1), (b2) or (b3) may be exemplified by DNA consisting of the nucleotide sequence shown in SEQ ID NO: 7, and DNA hybridizable under stringent conditions with DNA complementary to DNA consisting of the nucleotide sequence shown in SEQ ID NO: 7, etc. Such DNA hybridizable under stringent conditions with DNA complementary to DNA consisting of the nucleotide sequence shown in SEQ ID NO: 7 may be exemplified by DNA sharing a homology of at least 88% or more, preferably 90% or more, more preferably 95% or more with the DNA consisting of the nucleotide sequence shown in SEQ ID NO: 7. Such DNA hybridizable under stringent conditions with DNA complementary to DNA consisting of the nucleotide sequence shown in SEQ ID NO: 7 may also be exemplified by DNA consisting of the nucleotide sequence shown in SEQ ID NO: 11. The nucleotide sequence shown in SEQ ID NO: 11 is the nucleotide sequence of DNA encoding an amino acid sequence at positions 1-81 of the RNA polymerase PB1 subunit in influenza A virus (A/Duck/Hong Kong/2986.1/2000 (H5N1)).

"Stringent conditions" are the same as the conditions described above.

Examples of an expression vector available for use include *E. coli* plasmids (e.g., pBR322, pBR325, pUC12, pUC13), *Bacillus subtilis* plasmids (e.g., pUB110, pTP5, pC194), yeast plasmids (e.g., pSH19, pSH15), bacteriophages (e.g., λ phage), animal viruses (e.g., retrovirus, vaccinia virus), insect pathogenic viruses (e.g., baculovirus) and so on.

Such an expression vector may have a promoter, an enhancer, a ribosomal binding site, various signal sequences (e.g., splicing signal, poly(A) addition signal), a cloning site, a translation and/or transcription terminator, a selective marker, an SV40 replication origin, etc. Examples of such a vector include pGEX series (Amersham Pharmacia Biotech), pET Expression System (Novagen) and so on.

Examples of host cells include bacterial cells (e.g., *Escherichia* spp., *Bacillus* spp., *Bacillus subtilis*), fungal cells (e.g., yeast, *Aspergillus*), insect cells (e.g., S2 cells, Sf cells), animal cells (e.g., CHO cells, COS cells, HeLa cells, C127 cells, 3T3 cells, BHK cells, HEK293 cells), plant cells and so on.

Transfection of a recombinant vector into host cells may be accomplished by any method as described in Molecular Cloning 2nd Edition, J. Sambrook et al., Cold Spring Harbor Lab. Press, 1989 (e.g., calcium phosphate method, DEAE-dextran method, transvection, microinjection, lipofection, electroporation, transduction, scrape-loading method, shotgun method) or by infection.

Transformed cells carrying DNA encoding the polypeptide shown in (a1), (a2) or (a3) and DNA encoding the polypeptide shown in (b1), (b2) or (b3) can be cultured in a medium to thereby collect a complex between the polypeptide shown in (a1), (a2) or (a3) and the polypeptide shown in (b1), (b2) or (b3) from the cultured product. In a case where the complex is secreted into the medium, the medium may be collected and the complex may be separated and purified therefrom. In a case where the complex is produced within the transformed cells, the cells may be lysed and the complex may be separated and purified from the resulting lysate.

In a case where the complex is expressed in the form of a fusion protein with another protein (serving as a tag), the fusion protein may be separated and purified, followed by treatment with Factor Xa or an enzyme (enterokinase) to cleave another protein, thereby obtaining the desired complex.

Separation and purification of the complex may be accomplished in a known manner. Examples of known techniques used for separation and purification include those based on solubility (e.g., salting-out, solvent precipitation), those based on differences in molecular weight (e.g., dialysis, ultrafiltration, gel filtration, SDS-polyacrylamide gel electrophoresis), those based on differences in charge (e.g., ion exchange chromatography), those based on specific affinity (e.g., affinity chromatography), those based on differences in hydrophobicity (e.g., reversed-phase high performance liquid chromatography), those based on differences in isoelectric point (e.g., isoelectric focusing) and so on.

After being purified to have a purity sufficient for crystallization and then concentrated as needed, the complex can be crystallized in the presence of a precipitant. The present invention also provides a crystal of the complex. Examples of a precipitant include sodium formate. Techniques which can be used for crystallization include the batch method, the dialysis method, the vapor diffusion method and so on. In the case of using the batch method, crystallization is preferably accomplished by the hanging drop method. As an example, a crystal of the complex may have a space group of $P3_221$, and unit lattice of a=b=101.957±50.0 Å and c=115.023±50.0 Å.

The present invention also provides the polypeptide shown in (a1), (a2) or (a3), DNA encoding this polypeptide, a recombinant vector comprising this DNA, and a transformed cell carrying this DNA. Moreover, the present invention also provides a method for producing the polypeptide shown in (a1), (a2) or (a3), which comprises culturing a transformed cell carrying DNA encoding the polypeptide shown in (a1), (a2) or (a3), and collecting the polypeptide shown in (a1), (a2) or (a3) from the cultured product. Such a polypeptide, DNA, recombinant vector and transformed cell, and a production method thereof are defined in the same way as described above for the complex. The polypeptide shown in (a1), (a2) or (a3) may also be produced according to known peptide synthesis techniques.

Furthermore, the present invention also provides the polypeptide shown in (b1), (b2) or (b3), DNA encoding this polypeptide, a recombinant vector comprising this DNA, and a transformed cell carrying this DNA. Moreover, the present invention also provides a method for producing the polypeptide shown in (b1), (b2) or (b3), which comprises culturing a transformed cell carrying DNA encoding the polypeptide shown in (b1), (b2) or (b3), and collecting the polypeptide shown in (b1), (b2) or (b3) from the cultured product. Such a polypeptide, DNA, recombinant vector and transformed cell, and a production method thereof are defined in the same way as described above for the complex. The polypeptide shown in (b1), (b2) or (b3) may also be produced according to known peptide synthesis techniques.

The polypeptide shown in (a1), (a2) or (a3) and the polypeptide shown in (b1), (b2) or (b3) can be used in binding assay to screen anti-influenza virus agents.

In view of the fact that the RNA polymerase complex plays an essential role in viral transcription, replication and pathogenicity, its amino acid sequence is highly conserved across virus species. On the other hand, there is no homology with human proteins, and hence drugs targeting this complex are useful in that their side effects can be reduced.

(2) Screening Method for RNA Polymerase Inhibitors

In the second embodiment, the present invention provides a method for screening a substance capable of serving as an active ingredient in anti-influenza drugs, which comprises the steps of: allowing PA or a partial fragment thereof and PB1 or a partial fragment thereof, each of which constitutes influenza virus RNA polymerase, to contact with each other in the presence of a candidate substance; and selecting a substance which inhibits the interaction between the PA or partial fragment thereof and the PB1 or partial fragment thereof.

If the presence or absence of binding activity between PA and PB1 can be confirmed, it is possible to select a substance which inhibits the interaction between the subunits by the screening method of the present invention. Thus, as long as the PB1-binding site in PA is maintained, the amino acid sequence of PA may be mutated by deletion, substitution, addition or any combination thereof. It should be noted that the PA activity in this case does not always need to have polymerase activity upon binding between PA and PB1.

The presence or absence of binding activity between PA and PB1 can be detected in a known manner, for example, by immunoprecipitation, pull-down assay, etc.

In this embodiment, as described above, PA encompasses a protein which consists of an amino acid sequence mutated by deletion, substitution, addition or any combination thereof of one or several amino acids in the amino acid sequence shown in SEQ ID NO: 2 or a partial sequence thereof and which has the activity of RNA polymerase acidic subunit.

In this embodiment, examples of such an amino acid sequence mutated by deletion, substitution, addition or any combination thereof of one or several amino acids in the amino acid sequence shown in SEQ ID NO: 2 or a partial sequence thereof include:

(i) an amino acid sequence with deletion of 1 to 9 (e.g., 1 to 5, preferably 1 to 3, more preferably 1 to 2, even more preferably 1) amino acids from the amino acid sequence shown in SEQ ID NO: 2 or a partial sequence thereof;

(ii) an amino acid sequence with 1 to 9 (e.g., 1 to 5, preferably 1 to 3, more preferably 1 to 2, even more preferably 1) amino acids in the amino acid sequence shown in SEQ ID NO: 2 or a partial sequence thereof being substituted with other amino acids;

(iii) an amino acid sequence with addition of other 1 to 9 (e.g., 1 to 5, preferably 1 to 3, more preferably 1 to 2, even more preferably 1) amino acids to the amino acid sequence shown in SEQ ID NO: 2 or a partial sequence thereof; and (iv) an amino acid sequence mutated by any combination of (i) to (iii) above.

Moreover, in this embodiment, examples of PA variants include amino acid sequences which share a homology of about 80% or more, preferably 90% or more, more preferably about 95% or more, even more preferably about 98% or more with the amino acid sequence shown in SEQ ID NO: 2 or with the amino acid sequence of a partial sequence of SEQ ID NO: 2, and which have the activity of RNA polymerase acidic subunit.

Homology may be determined by using a homology search site on the Internet, for example, by homology search such as FASTA, BLAST, PSI-BLAST or the like in the DNA Data Bank of Japan (DDBJ).

It should be noted that Gln 408, Phe 411, Asn 412, Met 595, Glu 617, Thr 618, Trp 619, Pro 620, Ile 621, Glu 623, Val 636, Leu 640, Leu 666, Leu 667, Gln 670, Arg 673, Trp 706 and Phe 710, preferably Gln 408, Asn 412, Glu 617, Thr 618, Pro 620, Be 621, Glu 623, Gln 670 and Arg 673 in the amino acid sequence shown in SEQ ID NO: 2 are amino acids required to interact with PB1 and to form a binding pocket for PB1. Thus, to maintain the interaction activity with PB1, it is desired that any of the mutations described above does not occur in at least one amino acid residue selected from the group consisting of the amino acid residues listed above.

It should be noted that protein amino acid residues are represented herein either by their number alone, counting from the N-terminal end of the full-length amino acid sequence of each subunit, or by their number and their three letter code. In the latter case, for example, the glutamine residue at position 408 counted from the N-terminal end is indicated as "Gln 408" (the same applies hereinafter).

Procedures for mutagenesis are as described above.

PA also encompasses a protein which is encoded by the nucleotide sequence shown in SEQ ID NO: 1 or a partial sequence thereof, as well as a protein which is encoded by a polynucleotide hybridizable under stringent conditions with a polynucleotide consisting of a nucleotide sequence complementary to the nucleotide sequence shown in SEQ ID NO: 1 or a partial sequence thereof and which has the activity of RNA polymerase acidic subunit.

In the present invention, such a polynucleotide encoding PA is used for preparation of PA or variants thereof.

A polynucleotide hybridizable under stringent conditions is intended herein to encompass polynucleotides which comprise a nucleotide sequence sharing an identity (homology) of at least 80% or more, preferably 90% or more, more preferably 95% or more, even more preferably 97% or more with the nucleotide sequence shown in SEQ ID NO: 1 or a partial sequence thereof. A value representing identity can be calculated using a known program such as BLAST. Stringent conditions and hybridization procedures are the same as those described above.

In this embodiment, examples of a polynucleotide hybridizable under stringent conditions with a polynucleotide consisting of a nucleotide sequence complementary to the nucleotide sequence shown in SEQ ID NO: 1 or a partial sequence thereof include a polynucleotide which comprises a nucleotide sequence mutated, e.g., by deletion, substitution or addition of one or several nucleic acids in the nucleotide sequence shown in SEQ ID NO: 1 or a partial sequence thereof.

In this case, examples of such a polynucleotide which comprises a nucleotide sequence mutated, e.g., by deletion, substitution or addition of one or several nucleic acids in the nucleotide sequence shown in SEQ ID NO: 1 or a partial sequence thereof include:

(i) a nucleotide sequence with deletion of 1 to 10 (e.g., 1 to 5, preferably 1 to 3, more preferably 1 to 2, even more preferably 1) nucleic acids from the nucleotide sequence shown in SEQ ID NO: 1 or a partial sequence thereof;

(ii) a nucleotide sequence with 1 to 10 (e.g., 1 to 5, preferably 1 to 3, more preferably 1 to 2, even more preferably 1) nucleic acids in the nucleotide sequence shown in SEQ ID NO: 1 or a partial sequence thereof being substituted with other nucleic acids;

(iii) a nucleotide sequence with addition of other 1 to 10 (e.g., 1 to 5, preferably 1 to 3, more preferably 1 to 2, even more preferably 1) nucleic acids to the nucleotide sequence shown in SEQ ID NO: 1 or a partial sequence thereof; and (iv) a nucleotide sequence mutated by any combination of (i) to (iii) above.

If the presence or absence of binding activity between PA and PB1 can be confirmed, it is possible to select a substance which inhibits the interaction between the subunits by the screening method of the present invention. Thus, as long as at least the PA-binding site is maintained in PB1, the amino acid sequence of PB1 may be mutated by deletion, substitution, addition or any combination thereof. It should be noted that the PB1 activity in this case does not always mean having polymerase activity upon binding between PA and PB1.

The presence or absence of binding activity between PB1 and PA can be determined in a known manner, as described above.

In the context of the present invention, as described above, PB1 encompasses a protein which consists of an amino acid sequence mutated by deletion, substitution, addition or any combination thereof of one or several amino acids in the amino acid sequence shown in SEQ ID NO: 4 or a partial sequence thereof and which has the activity of RNA polymerase basic subunit.

Examples of such an amino acid sequence mutated by deletion, substitution, addition or any combination thereof of one or several amino acids in the amino acid sequence shown in SEQ ID NO: 4 or a partial sequence thereof include:

(i) an amino acid sequence with deletion of 1 to 9 (e.g., 1 to 5, preferably 1 to 3, more preferably 1 to 2, even more preferably 1) amino acids from the amino acid sequence shown in SEQ ID NO: 4;

(ii) an amino acid sequence with 1 to 9 (e.g., 1 to 5, preferably 1 to 3, more preferably 1 to 2, even more preferably 1) amino acids in the amino acid sequence shown in SEQ ID NO: 4 being substituted with other amino acids;

(iii) an amino acid sequence with addition of other 1 to 9 (e.g., 1 to 5, preferably 1 to 3, more preferably 1 to 2, even more preferably 1) amino acids to the amino acid sequence shown in SEQ ID NO: 4; and (iv) an amino acid sequence mutated by any combination of (i) to (iii) above.

Moreover, examples of PB1 variants include amino acid sequences which share a homology of about 80% or more, preferably 90% or more, more preferably about 95% or more, even more preferably about 98% or more with the amino acid sequence shown in SEQ ID NO: 4 or with the amino acid sequence of a partial sequence of SEQ ID NO: 4, and which have the activity of RNA polymerase β-subunit.

Met 1, Asp 2, Val 3, Asn 4, Pro 5, Thr 6, Leu 7, Leu 8, Phe 9, Leu 10, Lys 11, Val 12, Pro 13 and Ala 14 in the amino acid sequence shown in SEQ ID NO: 4 are amino acids required to interact with PA and to maintain binding with PA. Thus, it is desired that any of the mutations described above does not occur in at least one amino acid residue selected from the group consisting of the amino acid residues listed above.

Homology search may be accomplished by using a homology search site on the Internet, for example, by homology search such as FASTA, BLAST, PSI-BLAST or the like in the DNA Data Bank of Japan (DDBJ).

PB1 also encompasses a protein which is encoded by the nucleotide sequence shown in SEQ ID NO: 3 or a partial sequence thereof, as well as a protein which is encoded by a polynucleotide hybridizable under stringent conditions with a polynucleotide consisting of a nucleotide sequence complementary to the nucleotide sequence shown in SEQ ID NO: 3 or a partial sequence thereof and which has the activity of RNA polymerase basic subunit. In the present invention, such a polynucleotide encoding PB1 is used for preparation of PB1 or variants thereof.

With respect to other information about PB1, including procedures for site-directed mutagenesis, addition of a tag sequence, definition of stringent conditions, procedures for hybridization, embodiments of mutations, and conditions for PCR reaction, they are the same as those described above, except that the intended nucleotide sequence and amino acid sequence are SEQ ID NO: 3 and SEQ ID NO: 4, respectively.

In the context of the present invention, "interaction" between PA and PB1 is intended to mean that the constituent factors PA and PB1, which form a complex in the influenza virus RNA polymerase, are associated and bound to each other. The type of interaction includes, but is not limited to, hydrogen bonding, hydrophobic association, hydrophobic binding and so on.

The manner in which a candidate substance inhibits the interaction between PA and PB1 is not limited, and may include, for example, that the candidate substance may bind directly to the interaction site of PA or PB1 or that the candidate substance may bind to any site in PA or PB1 to thereby inhibit the interaction between these subunits.

In this context, the term "interaction" is intended to mean that PA and PB1, which form a complex, are associated and bound to each other.

The phrase "in the presence of a candidate substance" is intended to mean conditions that allow a test compound to contact with PA, PB1 or a complex thereof, which may be achieved by addition of a candidate compound to a reaction system containing PA or PB1 or a complex thereof, or by culturing cells containing PA or PB1 or a complex thereof (including cells into which genes for these elements are integrated in expressible form) in the presence of the candidate compound.

Candidate compounds to be screened are not limited, however preferred are compounds having affinity to PA or PB1.

In the context of the present invention, the term "interaction site" is intended to mean an amino acid sequence consisting of at least one amino acid residue among those exposed on the interface between PA and PB1.

Amino acid residues in the interaction site of PA are not limited as long as they are amino acid residues included in the amino acid sequence shown in SEQ ID NO: 2. However, preferred is at least one amino acid residue selected from the group consisting of Gln 408, Phe 411, Asn 412, Met 595, Glu 617, Thr 618, Trp 619, Pro 620, Be 621, Glu 623, Val 636, Leu 640, Leu 666, Leu 667, Gln 670, Arg 673, Trp 706 and Phe 710 listed above. More preferred is at least one amino acid residue selected from the group consisting of Val 636, Leu 640, Leu 666 and Trp 706.

Amino acid residues in the interaction site of PB1 comprise at least one amino acid residue selected from the group consisting of Met 1, Asp 2, Val 3, Asn 4, Pro 5, Thr 6, Leu 7, Leu 8, Phe 9, Leu 10, Lys 11, Val 12, Pro 13 and Ala 14 in the amino acid sequence shown in SEQ ID NO: 4. Preferred is at least one amino acid residue selected from the group consisting of Asn 4, Pro 5, Thr 6, Leu 7, Leu 8, Phe 9 and Leu 10 in the amino acid sequence shown in SEQ ID NO: 4.

Moreover, amino acid residues in the interaction site of PB1 are preferably amino acid residues 5-10 of the amino acid sequence shown in SEQ ID NO: 4.

In the context of the present invention, the term "contact" is intended to mean that cells modified to have genes encoding the above subunits and a candidate substance (test substance) are allowed to exist in the same reaction system or culture system, for example, by adding the candidate substance to a cell culture vessel, by mixing the cells with the candidate substance, or by culturing the cells in the presence of the candidate substance.

In this embodiment, the term "candidate substance" refers to any molecule capable of altering the RNA polymerase activity of influenza virus. Examples include naturally-occurring or synthetic compounds from a low-molecular-weight compound library, expression products (e.g., peptides, proteins) of a gene library, naturally-occurring or synthetic oligonucleic acids, naturally-occurring or synthetic peptides from a peptide library, antibodies, bacterial substances (e.g., substances released from bacteria by metabolism), microorganisms, plant cell extracts, animal cell extracts, compounds from cultured solutions (cultured products of microorganisms, plant cells, animal cells, etc.), compounds in soil, compounds contained in a phage display library, etc. Such compounds may be modified by conventional chemical, physical and/or biochemical means. For example, they can be converted into structural analogs by being subjected to direct chemical modification (e.g., alkylation, esterification, amidation) or random chemical modification.

Further, candidate compounds may also be those identified by pharmacophore search or with a computational structure comparison program. In the case of using such compounds identified by pharmacophore search or with a computational structure comparison program in the present invention, candidates for compounds that inhibit the interaction between PA and PB1 can be screened in silico, based on the results of structural analysis on the binding site between these subunits. In the Example section, as an in silico search for compounds, multiple target screening (MTS) whose hit rate is significantly higher than that of standard screening methods was used for screening.

The screening method of the present invention can be accomplished, for example, by biochemical procedures using PA- or PB1-producing cells or cell preparations thereof. Alternatively, at least one of PA and PB1 may be used in a purified form. Examples of "cell preparations" include cultured cells, homogenates of cultured cells, organella (e.g., cytoplasm, nuclei) fractionated from cultured cells, etc. Examples of PA- or PB1-producing cells include those used in standard genetic engineering procedures. For use in this purpose, these cells may be modified by gene transfer to express at least one of the PA and PB1 genes. Procedures for gene transfer are well known in the art and can be easily accomplished (see, e.g., Sambrook et al., Molecular Cloning, A Laboratory Manual 2nd ed., (Cold Spring Harbor Laboratory Press (1989)).

These compounds may be either novel or known, and may also be in salt form. The term "salt" refers to a pharmaceutically acceptable salt, and is not limited as long as pharmaceutically acceptable salts are formed with the above compounds. More specifically, preferred examples include halogenated hydroacid salts (e.g., hydrofluoride salt, hydrochloride salt, hydrobromide salt, hydroiodide salt), inorganic acid salts (e.g., sulfate salt, nitrate salt, perchlorate salt, phosphate salt, carbonate salt, bicarbonate salt), organic carboxylic acid salts (e.g., acetate salt, oxalate salt, maleate salt, tartrate salt, fumarate salt, citrate salt), organic sulfonic acid salts (e.g., methanesulfonate salt, trifluoromethanesulfonate salt, ethanesulfonate salt, benzenesulfonate salt, toluenesulfonate salt, camphorsulfonate salt), amino acid salts (e.g., aspartate salt, glutamate salt), quaternary amine salts, alkali metal salts (e.g., lithium salt, sodium salt, potassium salt), alkaline earth metal salts (e.g., magnesium salt, calcium salt) and so on.

To prepare PA and PB1, a gene encoding PA or PB1 (e.g., a gene having the nucleotide sequence shown in SEQ ID NO: 1 or 3 or a partial sequence thereof) may be adequately integrated into an expression vector to give a vector carrying the gene in a form suitable for expression of the encoded protein, and the resulting vector may be introduced into any of animal cells, plant cells, insect cells or microorganisms (e.g., yeast, E. coli) to give a transformant, followed by culturing the transformant thus obtained. Alternatively, their preparation may also be accomplished by using protein synthesis in a cell-free system. Protein synthesis in a cell-free system can be carried out using a commercially available kit, and examples of such a kit include reagent kits PROTEIOS™ (Toyobo Co., Ltd., Japan) and TNT™ System (Promega), as well as synthesizers PG-Mate™ (Toyobo Co., Ltd., Japan) and RTS (Roche Diagnostics), etc.

If desired, PA or PB1 produced in such a transformant or through protein synthesis in such a cell-free system may be separated and purified by various separation operations based on its physical properties, chemical properties, etc. Techniques used for purification may be exemplified by, for example, standard salting-out, centrifugation, ultrasonication, ultrafiltration, gel filtration, various liquid chromatographic techniques (e.g., ion exchange chromatography, affinity chromatography, high performance liquid chromatography (HPLC)), dialysis, or combinations thereof.

In another method for preparing PA or PB1, PA or PB1 may be produced in a form fused with an affinity tag in a transformant or through cell-free protein synthesis, followed by separation and purification.

The screening method of the present invention can be used to select a substance serving as an active ingredient in anti-influenza drugs by evaluating replication of influenza virus or transcription activity of its genome. Examples of assays using mammalian cells include those in a model viral replicon system which introduces a model viral genome and viral proteins related to transcription and replication (Turan, K. et al., Nucleic Acids Res. 29, 643-652 (2004)), as well as those in a virus infection system. Likewise, a model viral replicon system in yeast, for which genetic engineering procedures can be used, can also be adopted for the purpose of measuring transcription activity (International Publication No. WO2008/139627 A1). Further, it is also possible to use an in vitro viral genomic RNA synthesis system (Kawaguchi, A. and Nagata, K., EMBO J. 26, 4566-4575 (2007)). Those skilled in the art would be able to select an appropriate assay from those listed above to thereby construct a screening system that uses transcription activity as an index.

For use in the present invention, PA and PB1 can also be expressed as fusion proteins with a tag such as FLAG, HA, His, immunoglobulin Fc, GST, GFP, DsRed, Luciferase or Venus or with a labeled peptide. In this case, screening can be accomplished by immunoprecipitation or immunological procedures. The antibody used in these procedures may be an antibody recognizing such a tag. Instead of antibody immunoprecipitation, a Ni- or glutathione-immobilized solid layer (e.g., beads) may be used to capture a complex between PA and PB1. Further, the complex can also be detected using properties of the fused tag or peptide, i.e., enzyme activity or fluorescence activity. Furthermore, when the complex between PA and PB1 or a constituent factor thereof is detected, the constituent factor can be separated and detected by Western blotting.

When one of PA or PB1 is expressed as a fusion protein with a fluorescent protein such as GFP, a PA/PB1 complex may be captured on a solid layer with an antibody or the like that recognizes the molecule of the other subunit, and then directly measured for fluorescence activity to evaluate the interaction (binding state) between PA and PB1.

In these assays, the determination of whether a candidate substance inhibits binding between PA and PB1 may be accomplished, for example, by evaluation based on the absolute amount of inhibitory effect, evaluation based on comparison with a control, etc.

For example, in the evaluation based on comparison with a control, (i) PA and PB1 are brought into contact with each other in the presence and absence of a candidate compound, (ii) interaction between PA and PB1 is measured in both the presence and absence of the candidate compound, and (iii) a candidate compound affecting the interaction between PA and PB1 is selected based on the results measured in (ii) above.

The candidate compound selected in (iii) above is identified as a substance affecting the interaction between PA and PB1 or as an active ingredient in anti-influenza drugs.

According to the screening method of the present invention, any system which allows measurement of interaction (binding) between proteins can be used to search a substance inhibiting the desired interaction between PA and PB1. Such a measurement system may be either a cell-based or cell-free system, such as ELISA, RIA and other immunological procedures, as well as a two-hybrid system.

As a system for quantitative analysis of complex formation between PA and PB1, a technique such as pull-down assay or immunoprecipitation may be used, by way of example.

As a system for kinetic analysis of binding between PA and PB1, a technique based on surface plasmon resonance may also be used, by way of example. In this case, for example, a BIACORE™ protein interaction analysis system or the like may be used.

In a system for quantitative analysis of the interaction between PA and PB1, cells producing all of PA and PB1 or cell preparations thereof may be used for analysis.

(3) Screening Kit

PA and PB1 in the present invention can be provided in the form of a kit for use in screening a substance inhibiting their interaction or a substance capable of serving as an active ingredient in anti-influenza drugs. In addition to PA and PB1, the kit of the present invention may comprise other components such as a vector necessary for gene expression, a primer, a restriction enzyme, a labeling substance, a detection reagent and so on. The term "labeling substance" refers to an enzyme, a radioisotope, a fluorescent compound, a chemiluminescent compound or the like. In addition to the above components, the kit of the present invention may further comprise other reagents required to accomplish the method of the present invention, for example, an enzyme substrate (e.g., a chromogenic substrate), an enzyme substrate diluent, an enzyme reaction stop solution and so on in a case where the labeled product is an enzymatically labeled product. Furthermore, the kit of the present invention may also comprise a diluent for candidate compounds, various buffers, sterilized water, various cell culture vessels, various reaction vessels (e.g., Eppendorf tubes), a detergent, an instruction manual for experimental operations (manufacturer's instructions) and so on.

The present invention will be further described in more detail by way of the following illustrative examples, which are not intended to limit the scope of the invention.

1. Overview of Examples

Influenza A virus has a negative-strand RNA genome, which is divided into 8 segments. In its virion, each genome segment is bound to a single copy of the virally encoded RNA-dependent polymerase (Elton, D., Digard, P., Tiley, L. & Ortin, J. in Current Topics in Influenza Virology (ed. Kawaoka, Y.) 1-92 (Horizon Scientific Press, Norfolk, 2005)). This plays numerous essential roles in viral replication and pathogenesis, including "cap-snatching," i.e., the cleavage of host cell pre-mRNA and the use of its cap for viral transcripts (Huang, T. S. et al, J. Virol. 64, 5669-5673 (1990); Deng, T. et al, J. Gen. Virol. 87, 3373-3377 (2006); and Plotch, S. J. et al, Cell 23, 847-858 (1981)). Although many studies have been conducted to determine the precise roles of each polymerase subunit, some of these studies require further discussion.

For example, contradictory evidence has been presented showing that either PB1 or PB2 has cap-snatching endonuclease activity (Li, M. L. et al, EMBO J. 20, 2078-2086 (2001); and Fechter, P. et al, J. Biol. Chem. 278, 20381-20388 (2003)). Since RNA polymerase is essential for viral gene expression and viral replication, it shares a high level of sequence conservation across strains. RNA polymerase is also functionally unrelated to human proteins and hence serves as an appealing drug target. Currently, there is very limited structural information for this complex, and only the following are known. A 23 Å resolution reconstruction of the overall structure by electron microscopy shows a compact shape with no obvious domain boundaries (Area, E. et al., Proc. Natl. Acad. Sci. USA 101, 308-313 (2004); and Torreira, E. et al., Nucleic Acids Res. 35, 3774-3783 (2007)). The C-terminal domain of PB2 including its nuclear localization signal has been crystallized, in complex with importin α (Tarendeau, F. et al., Nature Struct. Mol. Biol. 14, 299-233 (2007)). Further, subunit interactions in RNA polymerase have been characterized by extensive mutagenesis, indicating that the N-terminal tip of PB1 binds to the C-terminal end of PA (Zurcher, T. et al, J. Gen. Viol. 77, 1745-1749 (1996); Perez, D. R. & Donis, R. O., J. Viol. 75, 8127-8136 (2001); and Ohtsu, Y. et al., Microbiol. Immunol. 46, 167-175 (2002)). Moreover, although PB1 shows many interactions with PB2, the loss of PA abolishes RNA polymerase activity (Kawaguchi, A. et al., J. Virol. 79, 732-744 (2005)). PA is necessary not only for complex stability, but also for endonuclease activity, cap binding and virion RNA (vRNA) promoter activity (Hara, K. et al., J. Virol. 80, 7789-7798 (2006)).

As a result of tryptic digestion, it was turned out that PA forms two domains (Hara, K. et al., J. Virol. 80, 7789-7798 (2006)). The C-terminal domain (residues 239-716) carrying the PB1 binding site was overexpressed alone in *E. coli* and then purified. Pull-down assays were used to confirm that this protein was capable of binding to PB1 and its C-terminal region (residues 657-716) was required for this interaction. This is consistent with the reports of Zurcher et al. (Zurcher, T. et al, J. Gen. Viol. 77, 1745-1749 (1996)) and Ohtsu et al. (Ohtsu, Y. et al., Microbiol. Immunol. 46, 167-175 (2002)). The binding region in PB1 has been defined by Perez et al., showing that its N-terminal 12 amino acids constitute a region essential for interaction (Perez, D. R. & Donis, R. O., J. Viol. 75, 8127-8136 (2001)). Co-expression of PA(239-716) and PB1(1-81) resulted in a stable complex which could be purified. Similar results were also obtained when PB1 was truncated to the N-terminal 14 or 36 residues. Thus, an attempt was made to crystallize these complexes, thereby obtaining a diffraction crystal of PA(239-716)/PB1(1-81).

Example 1

Figure 9:
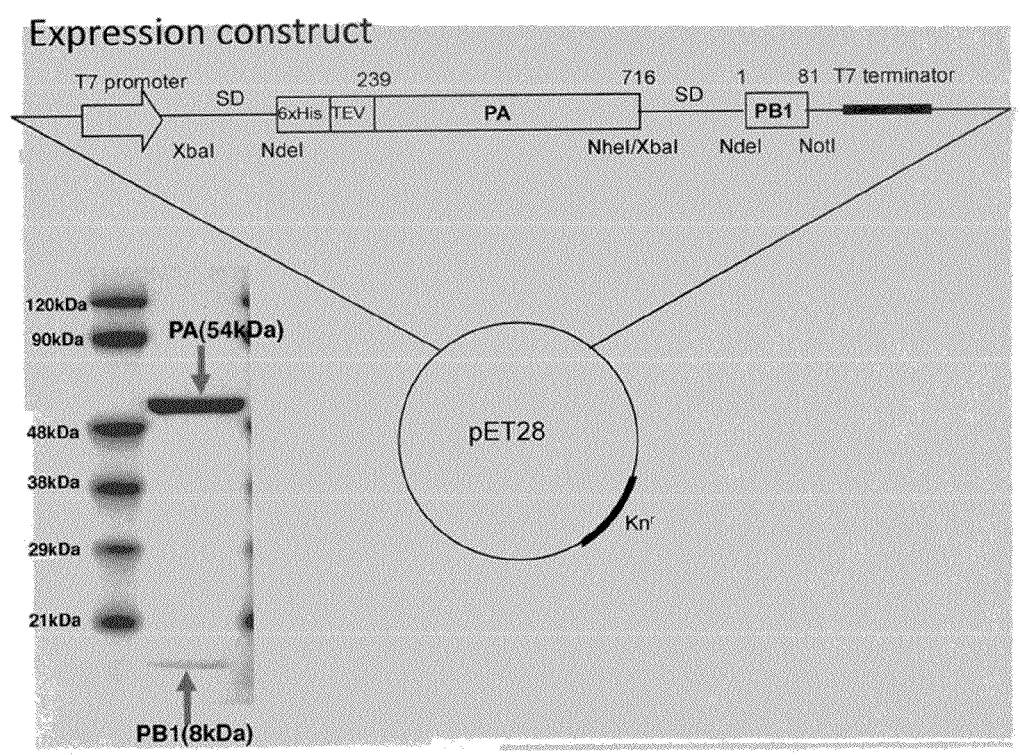

1. Materials and Methods (1) Cloning, Expression and Purification of PA-PB1 Complex To construct a protein expression system for use in this study, the influenza A/Puerto Rico/8/1934 (also referred to as "A/PR/8/34") H1N1 gene (cDNA (influenza A/PR/8/34, H1N1) in pET14b) was used. A gene encoding amino acids 239-716 of the RNA polymerase PA subunit was amplified by PCR, digested with restriction enzymes BamHI and NotI, and then integrated into a protein expression vector, pET28b (Novagen), which had been digested with the same enzymes. In this case, a histidine tag was integrated N-terminal to PA in order to facilitate protein purification, and a TEV protease cleavage sequence was integrated between the histidine tag and PA in order to remove this tag after purification (pET28HisTEV-PA(239-716)). Separately, a gene encoding amino acids 1-81 of the PB1 subunit was amplified by PCR, digested with restriction enzymes NdeI and NotI, and then integrated into a protein expression vector, pET21b, which had been digested with the same enzymes (pET21b-PB1(1-81)). Subsequently, a region covering the SD sequence necessary for protein expression and PB1(1-81) was excised with restriction enzymes XbaI and NotI from pET21b-PB1(1-81), and then integrated between restriction sites NheI and NotI in pET28HisTEV-PA(239-716) prepared above to thereby construct a PA-PB1 co-expression system (pET28HisTEV-PA(239-716)-PB1(1-81)) (FIG. 9). It should be noted that the NheI restriction site in pET28HisTEV-PA(239-716) had been integrated between the translation termination site of PA and the NotI restriction site during PCR amplification of the PA subunit gene.

pET28HisTEV-PA(239-716)-PB1(1-81) thus constructed was transformed into an *E. coli* strain for protein expression, BL21(DE3)RILP (Stratagene), which was then cultured in LB medium. IPTG was added at 0.5 mM to induce protein expression, followed by overnight culture at 15° C. The *E. coli* cells were collected and suspended in Ni-NTA-500 cell lysis solution (20 mM Tris pH 8.0, 500 mM NaCl, 500 mM urea, 25 mM imidazole and 10 mM β-mercaptoethanol), followed by ultrasonication to crush the cells. The insoluble fraction was removed by centrifugation, and the desired RNA polymerase PA-PB1 was purified using a Ni-NTA affinity column. To this, TEV protease was added to cleave the histidine tag from PA, and the Ni-NTA affinity column was used again to isolate PA-PB1 having no affinity tag. Further purification was performed with Q-sepharose to give a sample of sufficient purity for crystallization.

PA variant genes encoding PA amino acid sequences with a mutation from Val 636 to Ser, from Leu 640 to Glu, from Leu 666 to Glu, or from Trp 706 to Ala in the wild-type PA gene were also cloned in the same manner. These site-directed mutations were introduced by PCR. The resulting mutated proteins were purified in the same manner as described above.

(2) Crystal Analysis

For use in crystallization, PA (residues 239-716)-PB1 (residues 1-81) was concentrated to 15 mg/ml. Crystallization was performed by hanging drop vapor diffusion to obtain a crystal of PA-PB1 under conditions of 100 mM Tris-HCl (pH 7.5) and 2.4 M sodium formate. The heavy atom-substituted crystal used to obtain phase information was prepared by soaking the crystal obtained above into 0.5 mM thimerosal (Hg) for 12 hours.

These crystals were of space group $P3_221$, with a=b=101.957 Å and c=115.023 Å, and contained one molecule in an asymmetric unit. The crystals flash-frozen in crystallization buffer containing 30% (v/v) glycerol were used to collect their diffraction data at −180° C. In the Photon factory in Tsukuba (Ibaraki, Japan), data from the native and mercury-derivatized crystals were collected at 1.0 Å and 1.008 Å, respectively, on beam-lines BL5A and 17A using an ADSC Quantum 314 CCD detector. The diffraction data were added up and evaluated with HKL2000 and SCALEPACK (Otwinowski, Z. & Minor, W., Methods Enzymol., 276, 307-326 (1997)). For general handling of the data used in evaluation, programs available from the CCP4 site (Collaborative Computational Project, Number 4., Acta Crystallogr. D Biol. Crystallogr. 50, 760-763 (1994)) were used.

The datasets of the native and mercury-derivatized crystals were used for SIR phasing.

The programs used were Patterson peak search programs SHELXD (Sheldrick, G. M. SHELXS86-Program for crystal structure solution (University of Gottingen, Germany, 1986)) and SOLVE (Terwilliger, T. C., Methods Enzymol., 374, 22-37 (2003)).

The SOLVE program was used to determine five mercury sites and initial phases. Solvent flattening by RESOLVE was used to improve phase accuracy. After density modification, electron density maps were prepared at a resolution of 3.2 Å. The maps were of high quality sufficient to trace most of the chains. Model building with COOT (Emsley, P. & Cowtan, K., Acta Crystallogr. D Biol. Crystallogr. 60, 2126-2132 (2004)) and TURBO-FRODO (Roussel, A. & Cambillau, C., in Silicon Graphics Geometry Partner Directory, 77-78 (Silicon Graphics, Mountain View, Calif., 1989)) and refinement with programs CNS (Brunger, A. T. et al., Acta Crystallogr. D Biol. Crystallogr. 54, 905-921 (1998)) and REFMAC (Murshudov G. N. et al., Acta Crystallogr. D 53, 240-255 (1997)) were performed in successive rounds. Solvent molecules were placed at positions where spherical electron peaks were found above $1.3\sigma$ in the |2Fo-Fc| map and above $3.0\sigma$ in the |Fo-Fc| map, and where stereochemically reasonable hydrogen bonds were allowed. The final model contained residues 257-348, 354-371, 398-549 and 558-716 of PA as well as residues 1-15 of PB1 protein. Structural evaluation was performed on the final model of the complex protein using PROCHECK (Laskowski, R. A. et al., J. Appl. Cryst., 26, 283-291 (1993)), indicating that 87.7% of the residues were in the most favorable regions of the Ramachandran plot, and no amino acid residues were in "disallowed" regions. The data collection and refinement statistics are summarized in Supplementary Table 1.

SUPPLEMENTARY TABLE 1

| Data collection and refinement | | |
|---|---|---|
| | thimerosal (Hg) | Native |
| Data collection statistics | | |
| Resolution range (Å) | 50.0-3.3(3.42-3.3) | 50.0-2.3(2.38-2.3) |
| Space group/Unit cell dimensions (Å) | $P3_221$/ a = b = 102.189, c = 115.504 | $P3_221$/ a = b =101.957, c= 115.023 |
| Reflections (Measured/Unique) | 79,211/10,216 | 265,489/30,749 |
| Completeness (%) | 94.3 (64.3) | 95.5 (85.8) |
| Rmerge (%)[a] | 6.7 (12.9) | 6.4 (37.1) |
| Redundancy | 7.7 | 8.6 |
| Mean <I/s(I)> | 17.7 | 13.2 |

SUPPLEMENTARY TABLE 1-continued

Data collection and refinement

| | thimerosal (Hg) | Native |
|---|---|---|
| Refinement Statistics | | |
| R-factor (%)/free R-factor (%)[b] | | 20.7/26.2 |
| bond lengths (Å)/bond angles (°) | | 0.032/2.7 |
| Number of water molecules | | 75 |
| Average B-factor (PA/PB1/water, Å$^2$) | | 51/44/45 |
| Ramachandran plot | | |
| residues in most favorable regions (%) | | 87.7 |
| residues in additional allowed regions (%) | | 11.8 |
| residues in generously allowed regions (%) | | 0.5 |

[a]Rmerge = S | I$_i$ − <I> |/SI$_i$, where I$_i$ is the intensity of an observation and <I> in the mean value for its unique reflection, and the summations are over all reflections. Values in parentheses are for highest-resolution shell.
[b]R-factor = S$_h$|Fo(h) − Fc(h)|/S$_h$Fo(h), where Fo and Fc are the observed and calculated structure factor amplitudes, respectively. The free R-factor was calculated with 5% of the data excluded from refinement.

(3) Pull-Down Assay

The same procedure as shown above was repeated to clone the PA gene and the PB1 gene, except that a primer designed to have a NdeI cleavage site in the same sequence as 23 nucleotides from the 5'-terminal end of the nucleic acid sequence shown in SEQ ID NO: 1 was used for reverse transcription reaction of the PA gene, and a primer designed to have a NdeI cleavage site in the same sequence as 22 nucleotides from the 5'-terminal end of the nucleic acid sequence shown in SEQ ID NO: 3 was used for reverse transcription reaction of the PB1 gene, and also except that during amplification using the reverse-transcribed PA and PB1 cDNAs as templates, the same primer as used for reverse transcription reaction of the PA gene and a primer designed to have a BamHI site in a sequence complementary to 21 nucleotides from the 3'-terminal end of the nucleic acid sequence shown in SEQ ID NO: 1 were used for PA amplification, and the same primer as used for reverse transcription reaction of the PB1 gene and a primer designed to have a XhoI site in a sequence complementary to 21 nucleotides from the 3'-terminal end of the nucleic acid sequence shown in SEQ ID NO: 3 were used for PB1 amplification.

The synthesized gene for N-terminal residues 1-14 of PB1 was cloned into another modified pET28b vector (pETGST-TEV) in which a GST tag had been cloned instead of the histidine tag in pET28HisTEV. After expression in the same manner as used for the above PA-PB1 complex, GST-fused PB1(1-14) was purified with a 0-20 mM linear gradient of reduced glutathione in 20 mM Tris pH 8.0 using glutathione sepharose equilibrated with 150 mM NaCl and 5 mM DTT. For PA, cloning and purification were performed in the same manner as used for the PA-PB1 complex.

Two nmol of GST-tagged PB1 was incubated overnight at room temperature with 4 nmol of untagged PA in reconstitution buffer containing 20 mM Tris/HCl pH 8.0, 150 mM NaCl and 5 mM DTT. Then, 20 µl glutathione sepharose resin was used for pull-down of proteins. After the washing step with the same buffer as used for reconstitution, the complex was eluted with 50 µl elution buffer containing 20 mM reduced glutathione in the above buffer. Proteins were analyzed by SDS-acrylamide gel electrophoresis on a tris-glycine gel (5-20% gradient) and Coomassie blue staining.

2. Results (1) Results of Crystal Analysis

Figure 2:
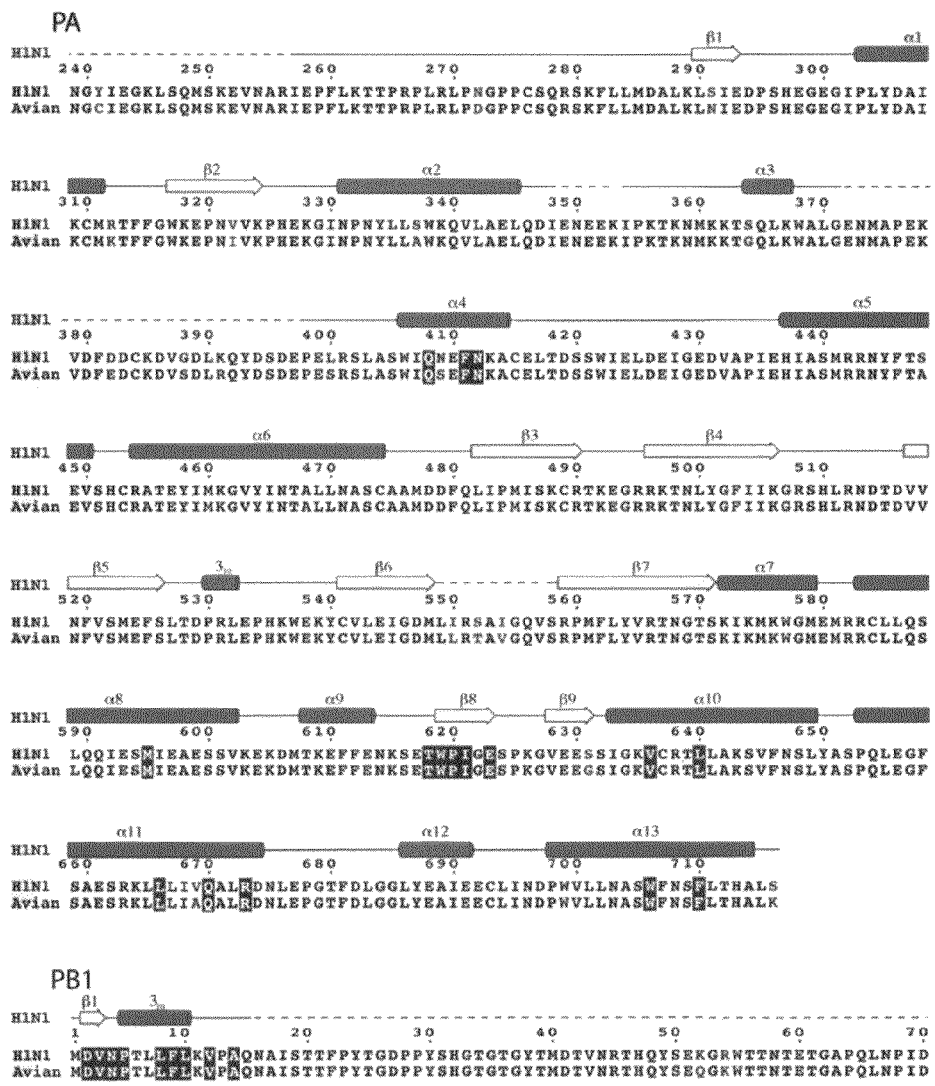
Figure 8:
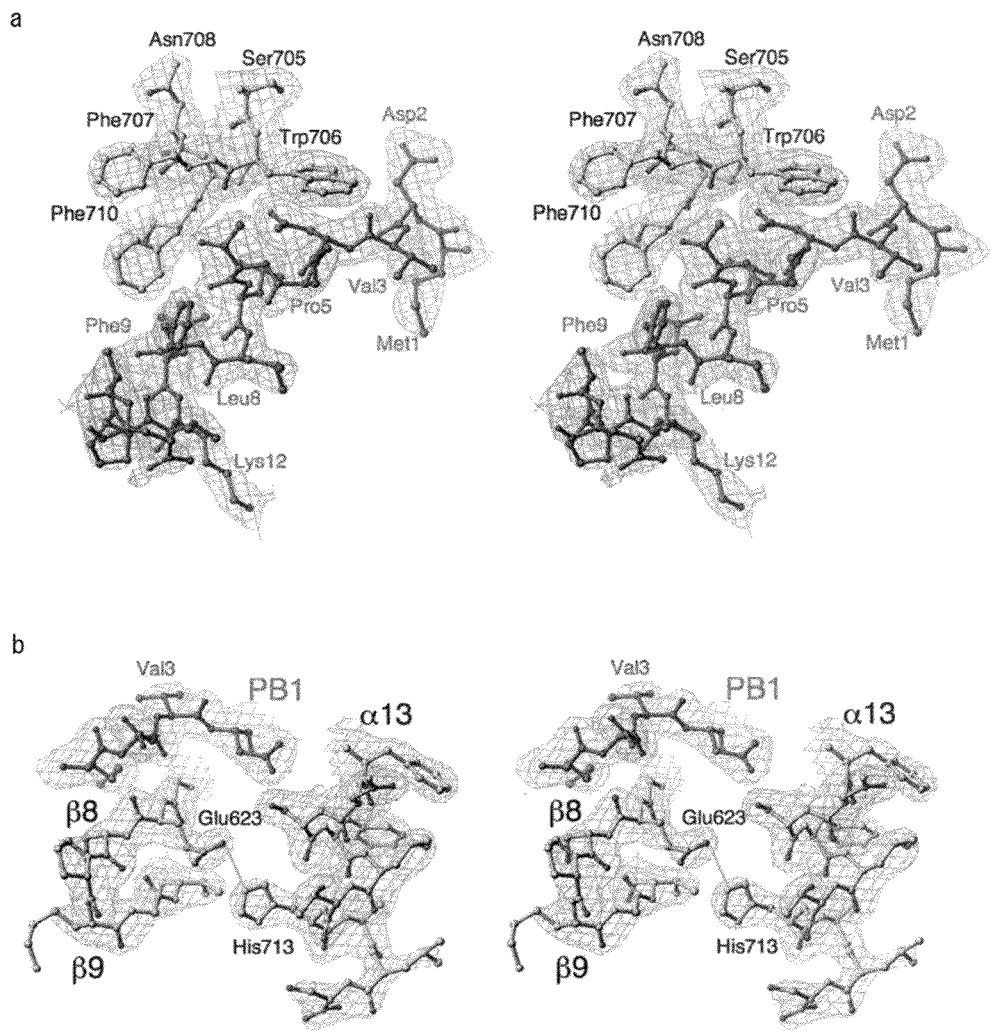

Native X-ray diffraction data were collected to 2.3 Å and the structure was analyzed using the single mercury-soaked crystal, indicating that the C domain of PA was composed of 13 α-helixes and 9 β-strands (FIGS. 1a and 1b). The N-terminal 18 residues and a loop between α3 and α4 (residues 372-397) are disordered, and hence PA in the final model consists of 423 amino acid residues in total, beginning with Ile 257. Three α-helixes (α10, α11, α13) in PA take a conformation similar to "jaws of clamp," and capture the N-terminal end of PB1 together with a β-hairpin loop formed by β8 and β9 (FIG. 1b). Upon PDB search with SSM (Secondary Structure Matching), there was no similar structure. This domain alone cannot bind to RNA and its surface has no especially highly charged region (FIG. 6a). The three C-terminal α-helixes (α10, α11 and α13) are positioned like the jaws of a clamp and grasp the N-terminal end of PB1 with the support of the β-hairpin loop formed by β8 and β9 (FIGS. 1a and 1b). Overall 15 residues, from Met 1 to Gln 15, of PB1 can be confirmed in the electron density map (FIG. 8a). An amino acid sequence consisting of these 15 amino acid residues is completely conserved in human and avian influenza (FIG. 2). In FIG. 2, amino acid residues shown in red represent amino acid residues which are not conserved between human and avian influenza. Amino acid residues shown in white on blue represent residues which form hydrogen bonds between PA and PB1. Amino acid residues shown in white on red represent residues which form hydrophobic contacts between PA and PB1. Blue bars represent α-helixes, yellow arrows represent β-strands, and broken lines represent removed amino acid residues.

Figure 5:
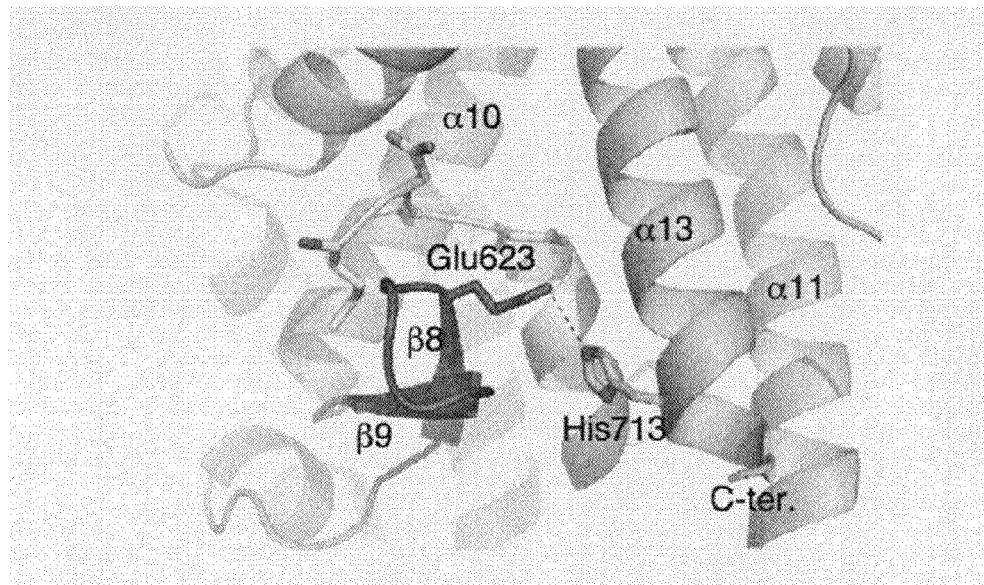

Met 1 and Asp 2 of PB1 emerge from a gap near the hairpin loop and are highly exposed to the solvent, whereas the side chain of Val 3 is partially buried (FIGS. 5 and 8b). Pro 5 to Lys 11 form a 3$_{10}$ helix, which is held by the finger-like clasp of PA. Pro 13 turns the main chain, so that Ala 14 and Gln 15 are packed into PA, but no further residues appear ordered in the structure. Crystals were grown by using a short PB1 bound to PA, but their diffraction was weak and could not be used for data collection. Mass spectrometry confirmed that all of the 81 residues in the PB1-derived peptide were present in the crystals, but most of them were invisible in the electron density map.

Figure 3:
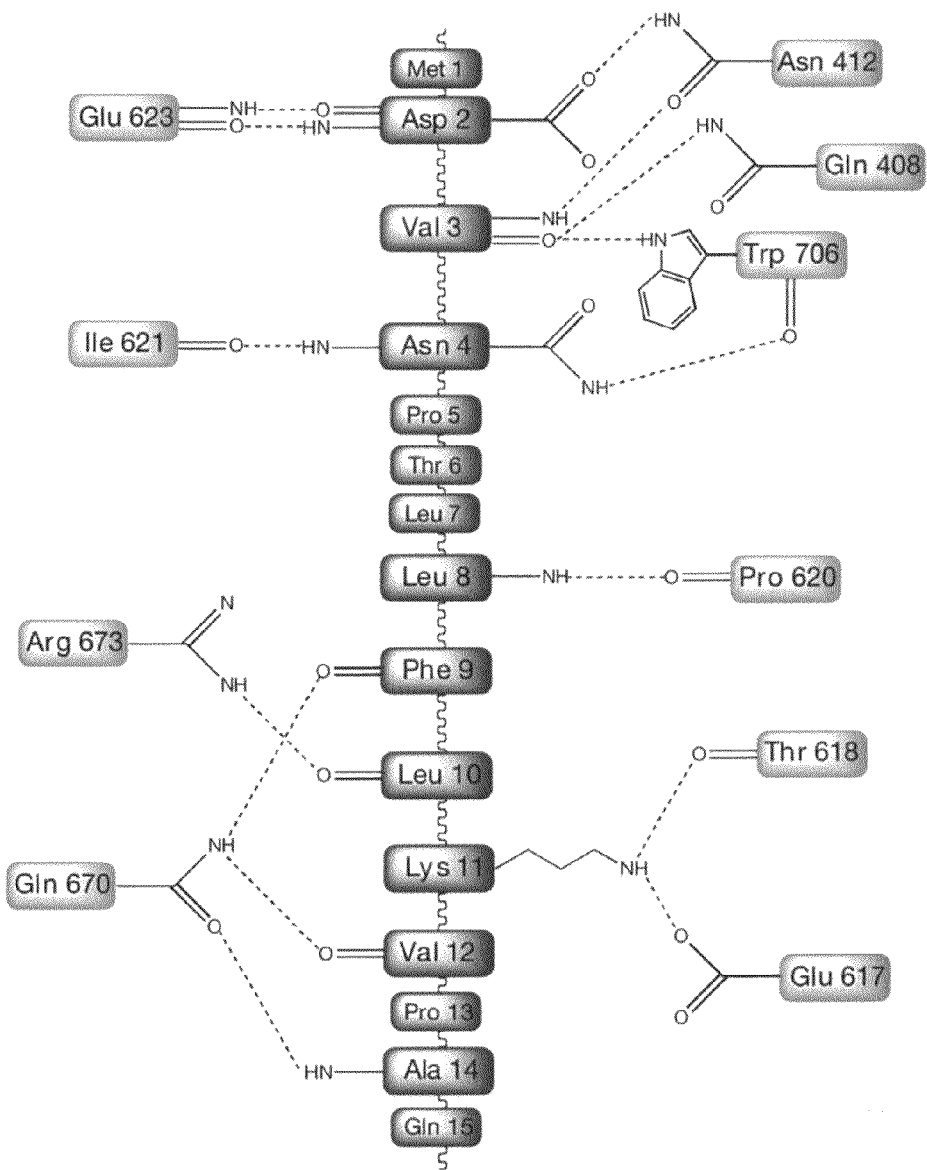
Figure 4:
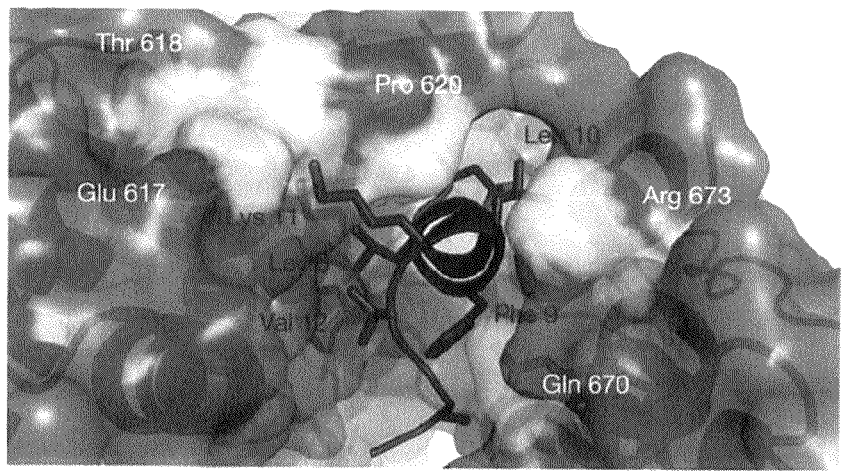
Figure 4:
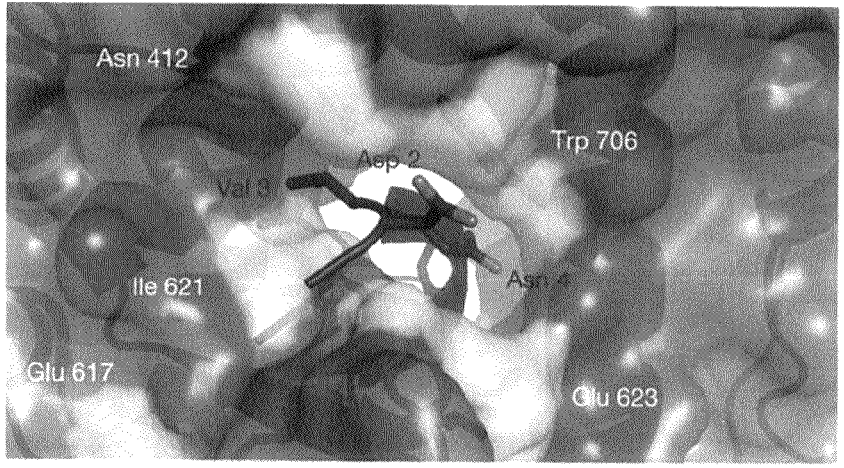
Figure 6:
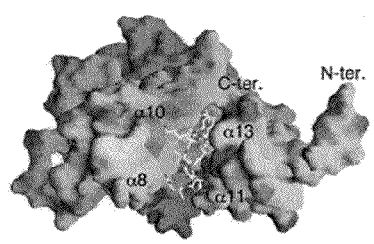
Figure 6:

PB1 interacts with PA at various regions through hydrogen bonding (FIGS. 3 and 4) and hydrophobic contact (FIGS. 6 and 7a). Moreover, most of the hydrogen bonds between these subunits are formed through main chain atoms of PB1 (FIGS. 3 and 4). In FIG. 4, Panel a shows amino acid binding sites on the PA surface. Amino acid residues which form hydrogen bonds with PB1 are shown in yellow, and the other regions are shown in blue. PB1 is shown in red Cα trace. This red Cα trace is shown in stick form, and nitrogen and oxygen atoms in the amino acid residues are shown in blue and pink, respectively. Panel b shows the same model as shown in Panel a, which is rotated by 180° around the vertical axis to show the N-terminal end of PB1. Met 1 and Asp 2 of PB1 emerge outside from a gap near the hairpin loop and are exposed to the solvent, whereas the side chain of Val 3 is partially buried (FIG. 4). Thus, even when N-acetylated, Met 1 would be less likely to form strong interactions with PA.

Figure 7:
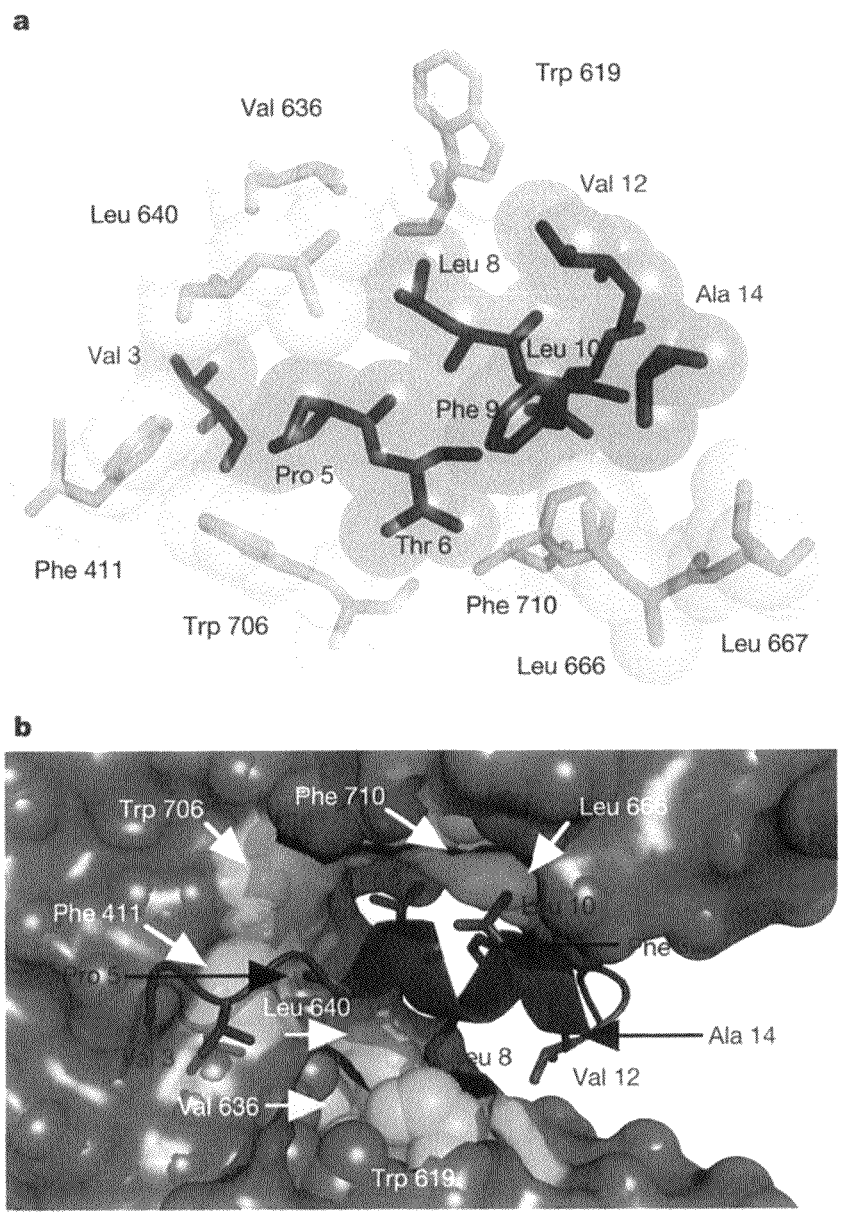

Most of the hydrogen bonds between the subunits are formed through main chain atoms of PB1. In FIG. 3, broken lines represent hydrogen bonds of 2.4-3.4 Å in length. Red-boxed amino acid residues (Met 1, Asp 2, Val 3, Asn 4, Pro 5, Thr 6, Leu 7, Leu 8, Phe 9, Leu 10, Lys 11, Val 12, Pro 13, Ala 14 and Gln 15) arranged in single file in the center of FIG. 3 are amino acid residues of PB1, while blue-boxed amino acid residues (Gln 408, Asn 412, Glu 617, Thr 618, Pro 620, Ile 621, Glu 623, Gln 670, Arg 673 and Trp 706) found at the both sides are amino acid residues of PA. Residues Asp 2 to Asn 4 in PB1 form anti-parallel β-sheet-like interactions with Be 621 to Glu 623 of PA. Moreover, the carbonyl oxygen atoms of Asp 2, Val 3, Phe 9, Leu 10 and Val 12 in PB1 form hydrogen bonds with Glu 623, Gln 408, Trp 706, Gln 670 and Arg 673 of PA. Likewise, the nitrogen atoms of Asp 2, Val 3, Asn 4, Leu 8 and Ala 14 in PB1 form hydrogen bonds with Glu 623, Asn 412, Be 621, Pro 620 and Gln 670, respectively (FIG. 3). Hydrophobic interactions appear to contribute substantially to binding energy (FIG. 7). In FIG. 7, Panel a is a space-filling representation showing hydrophobic contacts between PA and PB1. PA amino acid residues (Trp 619, Val 636, Leu 640, Phe 411, Trp 706, Phe 710, Leu 666 and Leu 667) are shown in green, while PB1 amino acid residues (Val 3, Pro 5, Thr 6, Leu 8, Phe 9, Leu 10, Val 12 and Ala 14) are shown in red. Panel b is a diagram showing the interface between PA and PB1, with the 138 and 139 strands being removed. In the molecular surface of PA, residues (Phe 411, Trp 619, Val 636, Leu 640, Leu 666, Trp 706, Phe 710) which form hydrophobic contacts (3.5-4.3 Å in length) with PB1 are shown in green, and the other residues are shown in blue. PB1 is shown in red. Pro 5 is packed between Ile 621 and Trp 706, and Leu 8 contacts with the side chains of Met 595, Trp 619, Val 636 and Leu 640 (FIG. 7a). Although the interface between PA and PB1 is almost tightly packed, unfilled spaces are found near Pro 5, Thr 6 and Phe 9 of PB1. The absence of any contact between Thr 6 of PB1 and PA suggests that substitution of the amino acid residue at this position would induce interactions with the adjacent side chains of Leu 666 and Phe 710. Leu 666 is pressed against the benzene ring of Phe 9 at a distance of 3.6 Å.

(2) Results of Pull-Down Assay

Using the above model, the inventors of the present invention designed deletions and single site mutations in the C-terminal domain of PA to study whether they would reduce or abolish the binding of PA to PB1 and whether they would reduce viral RNA synthesis in human cells (FIG. 10a).

To determine an amino acid sequence affecting the interaction between PA and PB1, wild-type (WT) PA and variants thereof were tested by pull-down assay for their binding to GST-fused N-terminal 14 residues of PB1 (FIG. 10b, middle). As a negative control, a sample of GST alone was used (FIG. 10b, bottom).

Figure 10:
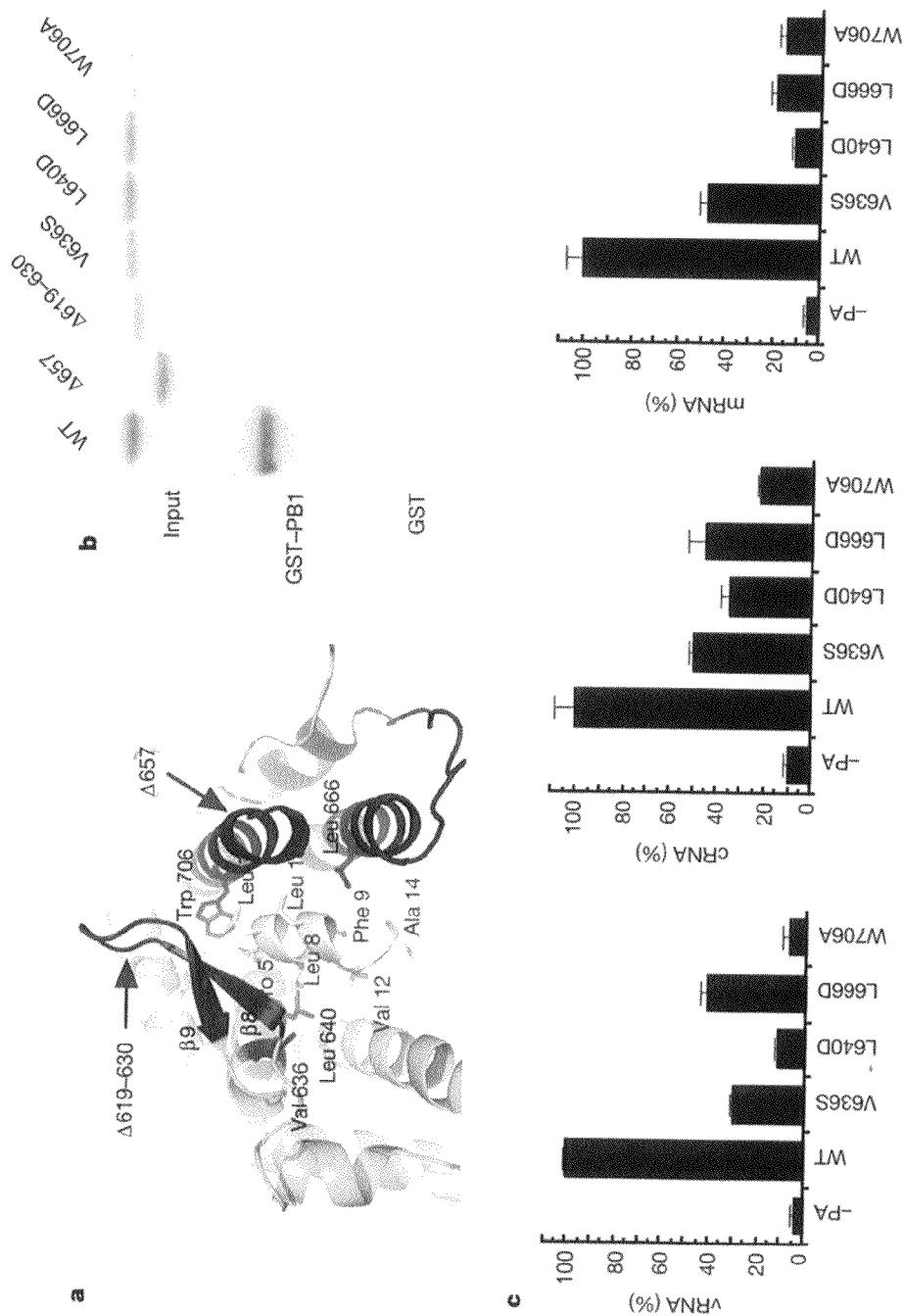
Figure 11:
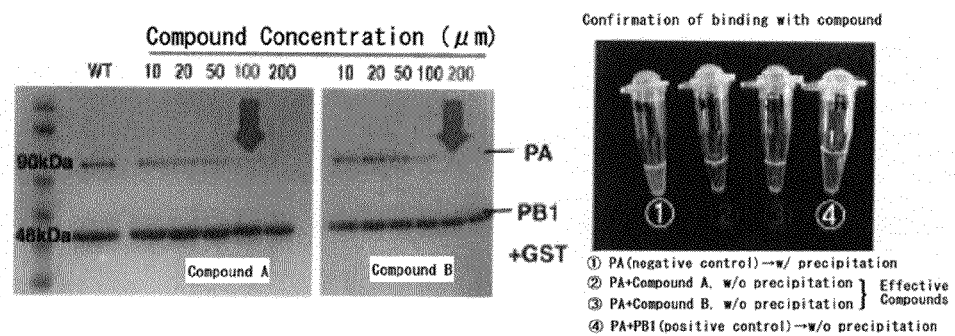
FIG. 11 shows an example of the results obtained from compound screening by biochemical procedures.
Figure 12:
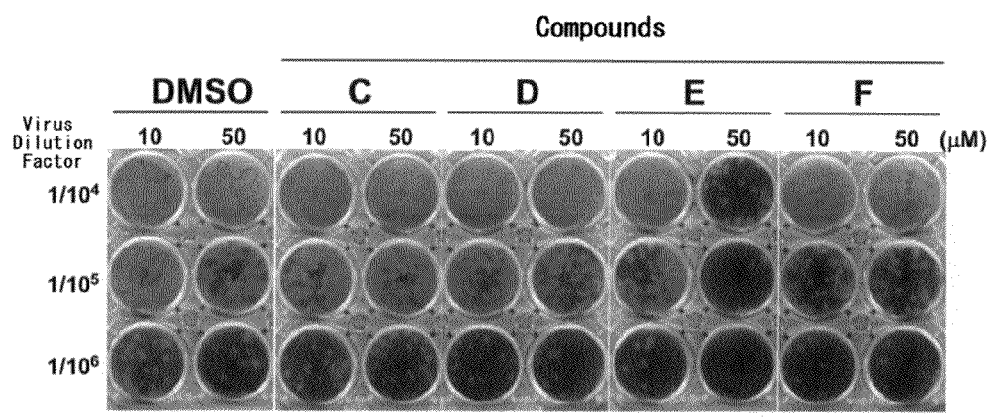
FIG. 12 shows an example of the results obtained from compound screening in a virus infection system.

In FIG. 10, Panel a is a model representation showing PA variants. Cα trace of PA is shown in green, and amino acid residues selected for mutation or deletion are shown in blue. PB1 is shown in yellow and its amino acid residues are labeled in red.

Panel b shows the results of GST pull-down assay on wild-type (WT) PA and various PA variants (Δ657, Δ619-630, V636S, L640D, L666D, W706A). The top row (input) shows electrophoretic patterns of various PA samples (wild-type (WT) PA or PA variants) which were not contacted with PB1, and the middle row (GST-PB1) shows electrophoretic patterns of various PA samples (wild-type (WT) PA or PA variants) which were contacted with PB1. The bottom row (GST) shows electrophoretic patterns of samples containing GST alone used as a negative control.

Panel c shows the effects of mutations in PA on the production levels of viral RNAs, as measured by quantitative PCR. In reporter assays, viral genomic RNA (vRNA), complementary RNA (cRNA) and viral mRNA were measured for their production levels. Experiments were performed independently in triplicate, and the results obtained are expressed as mean and standard deviation.

In FIG. 10a, Val 636 touches Leu 8, Leu 640 lies close to Leu 8 and Pro 5, and Leu 666 packs against the side chain of Phe 9. Trp 706 interacts with Asn 4, Pro 5 and Thr 6.

As a result, all of the tested deletion variants (Δ657, Δ619-630) and site-directed mutants of the C-terminal domain of PA (in which Val 636, Leu 640, Leu 666, Trp 706 and Phe 710 were replaced with V636S, L640D, L666D, W706A and F710A, respectively) had no ability to bind to PB1 (FIG. 10b).

Mutation from Pro 5 to leucine in PB1 abolished binding, suggesting that this residue not only makes an apolar contact with PA, but also helps to stabilize the helix. Replacement of either Val 3 or Thr 6 with Asp in PB1 caused a slight reduction in binding or maintained binding activity (by about 80% and 25%, respectively, in the assay used). This would be because these side chains in the above complex are accessible to water molecules in the solvent. Both Leu 7 and Leu 8 form many hydrophobic contacts, and their replacement with a charged side chain would be expected to destabilize the complex strongly. Although Phe 9 or Leu 10 does not apparently form as many interactions with PA as Leu 7 and Leu 8, and these residues are exposed to the solvent, replacement of either Phe 9 or Leu 10 with Asp completely inhibited PB1 binding. Probably, the aspartic acid side chain at position 9 of PB1 would hinder the helix of the N-terminal peptide. Similarly, carboxyl groups in this position would pull up adjacent Lys 643 or Arg 663 of PA to thereby distort the binding pocket. Since Leu 10 contacts with the side chain of Leu 7, its replacement with aspartic acid would interfere with key interactions formed by the residue. Asp 10 of the variant would almost certainly be pulled away by Arg 673. As discussed above, the overall crystal structure could provide a clear explanation on the behavior of the PB1 variants, so that the core of the PB1 interaction interface was restricted to five residues, i.e., Pro 5, Leu 7, Leu 8, Phe 9 and Leu 10. In the PA-PB1 complex, only the surface regions between these residues are packed (FIGS. 7a, 7b and 10a). In fact, the contribution of Phe 9 is considerably small, and strong PB1-PA binding would still be supported even when any functionally similar amino acid residue (e.g., leucine) is introduced in this position. Only the last two residues of the PTLLFL peptide sequence form hydrogen bonds with PA (FIG. 6).

The PA-binding site of PB1 is highly conserved, and its interaction is very important for many viral functions. Moreover, in consideration of the fact that this interaction relies on a few hydrophobic groups and hydrogen bonds, this binding site has a high potential as a drug target.

The peptide PTLLFL was found to be a lead molecule that assists the development of new treatments effective against all types of influenza A virus, including avian influenza.

Example 2

1. Materials and Methods (1) Reporter Assay for Measurement of Production Levels of Various Viral RNAs Viral transcription and replication were reconstituted in 293T cells by transfection with a plasmid carrying a fragment of the Luciferase gene whose 5'- and 3'-terminal ends were linked respectively to cDNAs of the viral genomic 3'- and 5'-terminal promoter sequences (26 and 23 nucleotides from the 3'- and 5'-terminal ends, respectively) under the control of the host DNA-dependent RNA polymerase I promoter and with a plasmid carrying viral genes (PB1, PB2, PA, NP) essential for transcription and replication of the viral genome under the control of the DNA-dependent RNA polymerase II promoter.

In this assay, the PA genes used were the wild-type PA gene, as well as PA variant genes encoding PA amino acid sequences with a mutation from Val 636 to Ser, from Leu 640 to Glu, from Leu 666 to Glu, or from Trp 706 to Ala in the wild-type PA gene. At 16 hours after transfection with the plasmids, the cells were collected and RNAs were purified.

Reverse transcription reaction was performed with the following primers: a primer having the same sequence as nucleotides 351-380 of the Luciferase gene for detection of viral genome; a primer having the same sequence as 5'-terminal 26 nucleotides of the viral genome for detection of intermediates in viral genome replication; and a primer having 20 nucleotides of T for detection of viral mRNA. The reverse-transcribed cDNAs were each used as a template for quantitative PCR in a Thermal Cycler Dice (TaKaRa) system using a primer having the same sequence as nucleotides 351-380 of the Luciferase gene and a primer complementary to nucleotides 681-700 of the Luciferase gene.

2. Results (1) Results of Reporter Assay

The same procedure was repeated to determine the relative expression levels of various viral RNAs for all the variants (Δ657, Δ619-630, V636S, L640β, L666β, W706β), indicating that the levels of vRNA, complementary RNA (cRNA) and viral mRNA synthesis were significantly decreased (FIG. 10*c*). In the absence of PA, the production level of each RNA is very low. Moreover, single site mutations also generally caused a reduction in the production level of each RNA by at least 40%.

Example 3

1. Materials and Methods (1) In Silico Search for Candidate Compounds

Based on the results of X-ray crystal structure analysis on the binding site between PA and PB1, the inventors of the present invention conducted an in silico search for candidate compounds capable of inhibiting the interaction between PA and PB1.

More specifically, two million compounds were divided into 200 groups of ten thousand each and calculated in parallel to search the compounds.

As a result, 5559 compounds were hit as candidate compounds through the in silico analysis.

Among the above 5559 compounds, 1298 compounds were determined to have a structure unsuitable for use as a drug. These compounds were excluded and the remaining 4261 compounds were able to be obtained as the final results of screening.

The selected compounds were purchased from Namiki Shoji Co., Ltd., Japan.

(2) Screening of Candidate Compounds

In this example, six compounds, i.e., Compounds A to F were used as candidate compounds.

These candidate compounds were subjected to the following assays to evaluate the functions of each compound.

(3) Biochemical Evaluation of Binding Between Polymerase Subunit and Candidate Compound As a biochemical method to evaluate the binding between polymerase subunit and candidate compound, co-precipitation was used to test the candidate compounds for their inhibition of the binding between PA and PB1.

Details are as follows.

A GST tag is fused to PB1 to precipitate PB1 using GST affinity resin. When this precipitation is performed in the presence of PA, both PA and PB1 will be precipitated because PA binds to PB1. Candidate compounds are expected to cause PA to lose its PB1 binding capacity through their binding to PA. Namely, this co-precipitation was performed in the presence of each candidate compound to confirm the presence or absence of inhibited binding between PA and PB1, thereby evaluating the candidate compound for its binding to PA.

(4) Physicochemical Evaluation of Binding Between Polymerase Subunit and Candidate Compound As a physicochemical method to evaluate the binding between polymerase subunit and candidate compound, isothermal titration calorimetry was used.

Details are as follows.

Changes in calorie upon addition of candidate compounds to the PA subunit alone are measured. Since a change in calorie will occur upon binding between candidate compound and PA, this change was measured to evaluate the binding between candidate compound and PA.

(5) Assay in Virus Infection System

To evaluate candidate compounds for their inhibitory effect on influenza virus replication, an assay in a virus infection system was used.

Details are as follows.

To a culture solution of mammalian cells, each candidate compound obtained by in silico analysis was added and influenza virus was then infected, followed by plaque assay (Kawaguchi, et al., J. Virol. 79, 732-744 (2005)) to quantify the amount of virus particles produced.

2. Results (1) Results of Biochemical Evaluation of Binding Between Polymerase Subunit and Candidate Compound Two compounds shown as Compounds A and B were confirmed to interact with the PA protein (FIG. 11).

(2) Results of Physicochemical Evaluation of Binding Between Polymerase Subunit and Candidate Compound As for the interaction with the PA protein, Compound A was found to have a dissociation constant (Kd) of 2 μM and 6 molecules were bound. Compound B showed about a 10-fold increase in Kd when compared to Compound A.

(3) Results of Assay in Virus Infection System

In some of the compounds, the amount of virus particles produced was reduced to 1/40, and inhibition of virus multiplication was observed (FIG. 12, Compound E).

The above examples indicated that a substance capable of serving as an active ingredient in anti-influenza drugs can be screened, by inhibiting the interaction between PA and PB1, which constitute the influenza virus RNA polymerase in the presence of candidate substances.

INDUSTRIAL APPLICABILITY

By the present invention, artificial large-scale purification of a complex between PA and PB1 of the influenza virus RNA polymerase protein became possible. Moreover, such a complex between PA and PB1 of the influenza virus RNA polymerase protein was identified for its structure and its amino acid residues essential for complex formation. Based on these findings, the present invention provides a method for screening a substance capable of serving as an active ingredient in anti-influenza drugs, independently of influenza strains and their mutations.

SEQUENCE LISTING FREE TEXT

<SEQ ID NO: 1>
SEQ ID NO: 1 shows the nucleotide sequence of DNA encoding the full-length RNA polymerase PA subunit in influenza A/Puerto Rico/8/1934 H1N1.
<SEQ ID NO: 2>
SEQ ID NO: 2 shows the amino acid sequence of the full-length RNA polymerase PA subunit in influenza A/Puerto Rico/8/1934 H1N1.
<SEQ ID NO: 3>
SEQ ID NO: 3 shows the nucleotide sequence of DNA encoding the full-length RNA polymerase PB1 subunit in influenza A/Puerto Rico/8/1934 H1N1.
<SEQ ID NO: 4>
SEQ ID NO: 4 shows the amino acid sequence of the full-length RNA polymerase PB1 subunit in influenza A/Puerto Rico/8/1934 H1N1.
<SEQ ID NO: 5>
SEQ ID NO: 5 shows the nucleotide sequence of DNA encoding residues 239-716 of the RNA polymerase PA subunit in influenza A/PUERTO RICO/8/1934 H1N1.
<SEQ ID NO: 6>
SEQ ID NO: 6 shows the amino acid sequence at positions 239-716 of the RNA polymerase PA subunit in influenza A/PUERTO RICO/8/1934 H1N1.
<SEQ ID NO: 7>
SEQ ID NO: 7 shows the nucleotide sequence of DNA encoding residues 1-81 of the RNA polymerase PB1 subunit in influenza A/PUERTO RICO/8/1934 H1N1.
<SEQ ID NO: 8>
SEQ ID NO: 8 shows the amino acid sequence at positions 1-81 of the RNA polymerase PB1 subunit in influenza A/PUERTO RICO/8/1934 H1N1.
<SEQ ID NO: 9>
SEQ ID NO: 9 shows the nucleotide sequence of DNA encoding residues 239-716 of the RNA polymerase PA subunit in influenza A virus (A/Duck/Hong Kong/2986.1/2000 (H5N1)).
<SEQ ID NO: 10>
SEQ ID NO: 10 shows the amino acid sequence at positions 239-716 of the RNA polymerase PA subunit in influenza A virus (A/Duck/Hong Kong/2986.1/2000 (H5N1)).
<SEQ ID NO: 11>
SEQ ID NO: 11 shows the nucleotide sequence of DNA encoding residues 1-81 of the RNA polymerase PB1 subunit in influenza A virus (A/Duck/Hong Kong/2986.1/2000 (H5N1)).
<SEQ ID NO: 12>
SEQ ID NO: 12 shows the amino acid sequence at positions 1-81 of the RNA polymerase PB1 subunit in influenza A virus (A/Duck/Hong Kong/2986.1/2000 (H5N1)).
<SEQ ID NO: 13>
SEQ ID NO: 13 shows a peptide sequence (PTLLFL) found in the RNA polymerase PB1 subunit in influenza A/PUERTO RICO/8/1934 H1N1.

The invention claimed is:

1. A purified polypeptide complex, wherein said complex possesses a polypeptide as set forth in (a1) or (a2) below and a polypeptide as set forth in (b1) or (b2) below:
   (a1) a polypeptide which consists of the amino acid sequence as set forth in SEQ ID NO: 6; or
   (a2) a polypeptide which consists of the amino acid sequence as set forth in SEQ ID NO: 6 wherein said polypeptide further possesses 1 to 10 deletions, substitutions or insertions, and has a biological activity of an RNA polymerase acidic subunit;
   And
   (b1) a polypeptide which consists of the amino acid sequence as set forth in SEQ ID NO: 8; or
   (b2) a polypeptide which consists of the amino acid sequence as set forth in SEQ ID NO: 8 wherein said polypeptide further possesses 1 to 10 deletions, substitutions or insertions, and has a biological activity of an RNA polymerase basic subunit.

2. A purified polypeptide as set forth in (a1) or (a2) below:
   (a1) a polypeptide which consists of the amino acid sequence as set forth in SEQ ID NO: 6; or
   (a2) a polypeptide which consists of the amino acid sequence as set forth in SEQ ID NO: 6 wherein said polypeptide further possesses 1 to 10 deletions, substitutions or insertions, and has a biological activity of an RNA polymerase acidic subunit.

3. The purified complex according to claim 1, wherein said complex is formed by polypeptides (a1) and (b1).

4. The purified polypeptide according to claim 2, which is (a1).

* * * * *

UNITED STATES PATENT AND TRADEMARK OFFICE
CERTIFICATE OF CORRECTION

PATENT NO. : 8,455,229 B2  
APPLICATION NO. : 13/001091  
DATED : June 4, 2013  
INVENTOR(S) : Kyosuke Nagata et al.

Page 1 of 1

It is certified that error appears in the above-identified patent and that said Letters Patent is hereby corrected as shown below:

ON THE TITLE PAGE:

At item (73), Assignee, change:

"(73) Assignee: University of Tsukuba, Tsukuba-Shi (JP)"

to

--(73) Assignees: University of Tsukuba, Tsukuba-shi (JP); Public University Corporation Yokohama City University, Yokohama-shi (JP)--.

Signed and Sealed this  
Twenty-sixth Day of November, 2013

Margaret A. Focarino  
*Commissioner for Patents of the United States Patent and Trademark Office*

SEQUENCE LISTING

```
<160> NUMBER OF SEQ ID NOS: 13

<210> SEQ ID NO 1
<211> LENGTH: 2151
<212> TYPE: DNA
<213> ORGANISM: Influenza A Virus
<220> FEATURE:
<221> NAME/KEY: CDS
<222> LOCATION: (1)..(2151)
<223> OTHER INFORMATION: PA of Influenza A/Puerto Rico/8/1934 H1N1

<400> SEQUENCE: 1 atg gaa gat ttt gtg cga caa tgc ttc aat ccg atg att gtc gag ctt        48
Met Glu Asp Phe Val Arg Gln Cys Phe Asn Pro Met Ile Val Glu Leu
1               5                   10                  15 gcg gaa aaa aca atg aaa gag tat ggg gag gac ctg aaa atc gaa aca        96
Ala Glu Lys Thr Met Lys Glu Tyr Gly Glu Asp Leu Lys Ile Glu Thr
                20                  25                  30 aac aaa ttt gca gca ata tgc act cac ttg gaa gta tgc ttc atg tat       144
Asn Lys Phe Ala Ala Ile Cys Thr His Leu Glu Val Cys Phe Met Tyr
            35                  40                  45 tca gat ttc cac ttc atc aat gag caa ggc gag tca ata atc gta gaa       192
Ser Asp Phe His Phe Ile Asn Glu Gln Gly Glu Ser Ile Ile Val Glu
        50                  55                  60 ctt ggt gat cct aat gca ctt ttg aag cac aga ttt gaa ata atc gag       240
Leu Gly Asp Pro Asn Ala Leu Leu Lys His Arg Phe Glu Ile Ile Glu
```

```
                65                  70                  75                  80
gga aga gat cgc aca atg gcc tgg aca gta gta aac agt att tgc aac        288
Gly Arg Asp Arg Thr Met Ala Trp Thr Val Val Asn Ser Ile Cys Asn
                    85                  90                  95 act aca ggg gct gag aaa cca aag ttt cta cca gat ttg tat gat tac        336
Thr Thr Gly Ala Glu Lys Pro Lys Phe Leu Pro Asp Leu Tyr Asp Tyr
                100                 105                 110 aag gaa aat aga ttc atc gaa att gga gta aca agg aga gaa gtt cac        384
Lys Glu Asn Arg Phe Ile Glu Ile Gly Val Thr Arg Arg Glu Val His
                115                 120                 125 ata tac tat ctg gaa aag gcc aat aaa att aaa tct gag aaa aca cac        432
Ile Tyr Tyr Leu Glu Lys Ala Asn Lys Ile Lys Ser Glu Lys Thr His
        130                 135                 140 atc cac att ttc tcg ttc act ggg gaa gaa atg gcc aca aag gcc gac        480
Ile His Ile Phe Ser Phe Thr Gly Glu Glu Met Ala Thr Lys Ala Asp
145                 150                 155                 160 tac act ctc gat gaa gaa agc agg gct agg atc aaa acc agg cta ttc        528
Tyr Thr Leu Asp Glu Glu Ser Arg Ala Arg Ile Lys Thr Arg Leu Phe
                165                 170                 175 acc ata aga caa gaa atg gcc agc aga ggc ctc tgg gat tcc ttt cgt        576
Thr Ile Arg Gln Glu Met Ala Ser Arg Gly Leu Trp Asp Ser Phe Arg
                180                 185                 190 cag tcc gag aga gga gaa gag aca att gaa gaa agg ttt gaa atc aca        624
Gln Ser Glu Arg Gly Glu Glu Thr Ile Glu Glu Arg Phe Glu Ile Thr
                195                 200                 205 gga aca atg cgc aag ctt gcc gac caa agt ctc ccg ccg aac ttc tcc        672
Gly Thr Met Arg Lys Leu Ala Asp Gln Ser Leu Pro Pro Asn Phe Ser
        210                 215                 220 agc ctt gaa aat ttt aga gcc tat gtg gat gga ttc gaa ccg aac ggc        720
Ser Leu Glu Asn Phe Arg Ala Tyr Val Asp Gly Phe Glu Pro Asn Gly
225                 230                 235                 240 tac att gag ggc aag ctg tct caa atg tcc aaa gaa gta aat gct aga        768
Tyr Ile Glu Gly Lys Leu Ser Gln Met Ser Lys Glu Val Asn Ala Arg
                245                 250                 255 att gaa cct ttt ttg aaa aca aca cca cga cca ctt aga ctt ccg aat        816
Ile Glu Pro Phe Leu Lys Thr Thr Pro Arg Pro Leu Arg Leu Pro Asn
                260                 265                 270 ggg cct ccc tgt tct cag cgg tcc aaa ttc ctg ctg atg gat gcc tta        864
Gly Pro Pro Cys Ser Gln Arg Ser Lys Phe Leu Leu Met Asp Ala Leu
        275                 280                 285 aaa tta agc att gag gac cca agt cat gaa gga gag gga ata ccg cta        912
Lys Leu Ser Ile Glu Asp Pro Ser His Glu Gly Glu Gly Ile Pro Leu
                290                 295                 300 tat gat gca atc aaa tgc atg aga aca ttc ttt gga tgg aag gaa ccc        960
Tyr Asp Ala Ile Lys Cys Met Arg Thr Phe Phe Gly Trp Lys Glu Pro
305                 310                 315                 320 aat gtt gtt aaa cca cac gaa aag gga ata aat cca aat tat ctt ctg       1008
Asn Val Val Lys Pro His Glu Lys Gly Ile Asn Pro Asn Tyr Leu Leu
                325                 330                 335 tca tgg aag caa gta ctg gca gaa ctg cag gac att gag aat gag gag       1056
Ser Trp Lys Gln Val Leu Ala Glu Leu Gln Asp Ile Glu Asn Glu Glu
                340                 345                 350 aaa att cca aag act aaa aat atg aaa aaa aca agt cag cta aag tgg       1104
Lys Ile Pro Lys Thr Lys Asn Met Lys Lys Thr Ser Gln Leu Lys Trp
        355                 360                 365 gca ctt ggt gag aac atg gca cca gaa aag gta gac ttt gac gac tgt       1152
Ala Leu Gly Glu Asn Met Ala Pro Glu Lys Val Asp Phe Asp Asp Cys
370                 375                 380 aaa gat gta ggt gat ttg aag caa tat gat agt gat gaa cca gaa ttg       1200
Lys Asp Val Gly Asp Leu Lys Gln Tyr Asp Ser Asp Glu Pro Glu Leu
```

```
                385                 390                 395                 400
agg tcg ctt gca agt tgg att cag aat gag ttc aac aag gca tgc gaa        1248
Arg Ser Leu Ala Ser Trp Ile Gln Asn Glu Phe Asn Lys Ala Cys Glu
                    405                 410                 415 ctg aca gat tca agc tgg ata gag ctt gat gag att gga gaa gat gtg        1296
Leu Thr Asp Ser Ser Trp Ile Glu Leu Asp Glu Ile Gly Glu Asp Val
                420                 425                 430 gct cca att gaa cac att gca agc atg aga agg aat tat ttc aca tca        1344
Ala Pro Ile Glu His Ile Ala Ser Met Arg Arg Asn Tyr Phe Thr Ser
            435                 440                 445 gag gtg tct cac tgc aga gcc aca gaa tac ata atg aag ggg gtg tac        1392
Glu Val Ser His Cys Arg Ala Thr Glu Tyr Ile Met Lys Gly Val Tyr
        450                 455                 460 atc aat act gcc tta ctt aat gca tct tgt gca gca atg gat gat ttc        1440
Ile Asn Thr Ala Leu Leu Asn Ala Ser Cys Ala Ala Met Asp Asp Phe
465                 470                 475                 480 caa tta att cca atg ata agc aag tgt aga act aag gag gga agg cga        1488
Gln Leu Ile Pro Met Ile Ser Lys Cys Arg Thr Lys Glu Gly Arg Arg
                485                 490                 495 aag acc aac ttg tat ggt ttc atc ata aaa gga aga tcc cac tta agg        1536
Lys Thr Asn Leu Tyr Gly Phe Ile Ile Lys Gly Arg Ser His Leu Arg
            500                 505                 510 aat gac acc gac gtg gta aac ttt gtg agc atg gag ttt tct ctc act        1584
Asn Asp Thr Asp Val Val Asn Phe Val Ser Met Glu Phe Ser Leu Thr
        515                 520                 525 gac cca aga ctt gaa cca cac aaa tgg gag aag tac tgt gtt ctt gag        1632
Asp Pro Arg Leu Glu Pro His Lys Trp Glu Lys Tyr Cys Val Leu Glu
    530                 535                 540 ata gga gat atg ctt cta aga agt gcc ata ggc cag gtt tca agg ccc        1680
Ile Gly Asp Met Leu Leu Arg Ser Ala Ile Gly Gln Val Ser Arg Pro
545                 550                 555                 560 atg ttc ttg tat gtg agg aca aat gga acc tca aaa att aaa atg aaa        1728
Met Phe Leu Tyr Val Arg Thr Asn Gly Thr Ser Lys Ile Lys Met Lys
                565                 570                 575 tgg gga atg gag atg agg cgt tgt ctc ctc cag tca ctt caa caa att        1776
Trp Gly Met Glu Met Arg Arg Cys Leu Leu Gln Ser Leu Gln Gln Ile
            580                 585                 590 gag agt atg att gaa gct gag tcc tct gtc aaa gag aaa gac atg acc        1824
Glu Ser Met Ile Glu Ala Glu Ser Ser Val Lys Glu Lys Asp Met Thr
        595                 600                 605 aaa gag ttc ttt gag aac aaa tca gaa aca tgg ccc att gga gag tct        1872
Lys Glu Phe Phe Glu Asn Lys Ser Glu Thr Trp Pro Ile Gly Glu Ser
    610                 615                 620 ccc aaa gga gtg gag gaa agt tcc att ggg aag gtc tgc agg act tta        1920
Pro Lys Gly Val Glu Glu Ser Ser Ile Gly Lys Val Cys Arg Thr Leu
625                 630                 635                 640 tta gca aag tcg gta ttt aac agc ttg tat gca tct cca caa cta gaa        1968
Leu Ala Lys Ser Val Phe Asn Ser Leu Tyr Ala Ser Pro Gln Leu Glu
                645                 650                 655 gga ttt tca gct gaa tca aga aaa ctg ctt ctt atc gtt cag gct ctt        2016
Gly Phe Ser Ala Glu Ser Arg Lys Leu Leu Leu Ile Val Gln Ala Leu
            660                 665                 670 agg gac aat ctg gaa cct ggg acc ttt gat ctt ggg gga cta tat gaa        2064
Arg Asp Asn Leu Glu Pro Gly Thr Phe Asp Leu Gly Gly Leu Tyr Glu
        675                 680                 685 gca att gag gag tgc cta att aat gat ccc tgg gtt ttg ctt aat gct        2112
Ala Ile Glu Glu Cys Leu Ile Asn Asp Pro Trp Val Leu Leu Asn Ala
    690                 695                 700 tct tgg ttc aac tcc ttc ctt aca cat gca ttg agt tag                    2151
Ser Trp Phe Asn Ser Phe Leu Thr His Ala Leu Ser
```

705             710             715

<210> SEQ ID NO 2
<211> LENGTH: 716
<212> TYPE: PRT
<213> ORGANISM: Influenza A Virus

<400> SEQUENCE: 2

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys 370              375              380
Lys Asp Val Gly Asp Leu Lys Gln Tyr Asp Ser Asp Glu Pro Glu Leu
385                      390                      395                      400

Arg Ser Leu Ala Ser Trp Ile Gln Asn Glu Phe Asn Lys Ala Cys Glu
                405                      410                      415

Leu Thr Asp Ser Ser Trp Ile Glu Leu Asp Glu Ile Gly Glu Asp Val
            420                      425                      430

Ala Pro Ile Glu His Ile Ala Ser Met Arg Arg Asn Tyr Phe Thr Ser
                435                      440                      445

Glu Val Ser His Cys Arg Ala Thr Glu Tyr Ile Met Lys Gly Val Tyr
450                      455                      460

Ile Asn Thr Ala Leu Leu Asn Ala Ser Cys Ala Ala Met Asp Asp Phe
465                      470                      475                      480

Gln Leu Ile Pro Met Ile Ser Lys Cys Arg Thr Lys Glu Gly Arg Arg
                485                      490                      495

Lys Thr Asn Leu Tyr Gly Phe Ile Ile Lys Gly Arg Ser His Leu Arg
                500                      505                      510

Asn Asp Thr Asp Val Val Asn Phe Val Ser Met Glu Phe Ser Leu Thr
            515                      520                      525

Asp Pro Arg Leu Glu Pro His Lys Trp Glu Lys Tyr Cys Val Leu Glu
530                      535                      540

Ile Gly Asp Met Leu Leu Arg Ser Ala Ile Gly Gln Val Ser Arg Pro
545                      550                      555                      560

Met Phe Leu Tyr Val Arg Thr Asn Gly Thr Ser Lys Ile Lys Met Lys
                565                      570                      575

Trp Gly Met Glu Met Arg Arg Cys Leu Leu Gln Ser Leu Gln Gln Ile
            580                      585                      590

Glu Ser Met Ile Glu Ala Glu Ser Ser Val Lys Glu Lys Asp Met Thr
        595                      600                      605

Lys Glu Phe Phe Glu Asn Lys Ser Glu Thr Trp Pro Ile Gly Glu Ser
610                      615                      620

Pro Lys Gly Val Glu Glu Ser Ser Ile Gly Lys Val Cys Arg Thr Leu
625                      630                      635                      640

Leu Ala Lys Ser Val Phe Asn Ser Leu Tyr Ala Ser Pro Gln Leu Glu
                645                      650                      655

Gly Phe Ser Ala Glu Ser Arg Lys Leu Leu Leu Ile Val Gln Ala Leu
            660                      665                      670

Arg Asp Asn Leu Glu Pro Gly Thr Phe Asp Leu Gly Gly Leu Tyr Glu
        675                      680                      685

Ala Ile Glu Glu Cys Leu Ile Asn Asp Pro Trp Val Leu Leu Asn Ala
690                      695                      700

Ser Trp Phe Asn Ser Phe Leu Thr His Ala Leu Ser
705                      710                      715

<210> SEQ ID NO 3
<211> LENGTH: 2274
<212> TYPE: DNA
<213> ORGANISM: Influenza A Virus
<220> FEATURE:
<221> NAME/KEY: CDS
<222> LOCATION: (1)..(2274)
<223> OTHER INFORMATION: PB1 of Influenza A/Puerto Rico/8/1934 H1N1

<400> SEQUENCE: 3 atg gat gtc aat ccg acc tta ctt ttc tta aaa gtg cca gca caa aat        48
Met Asp Val Asn Pro Thr Leu Leu Phe Leu Lys Val Pro Ala Gln Asn
1

| | | |
|---|---|---|
| gct ata agc aca act ttc cct tat act gga gac cct cct tac agc cat<br>Ala Ile Ser Thr Thr Phe Pro Tyr Thr Gly Asp Pro Pro Tyr Ser His<br>            20                       25                       30 | | 96 |
| ggg aca gga aca gga tac acc atg gat act gtc aac agg aca cat cag<br>Gly Thr Gly Thr Gly Tyr Thr Met Asp Thr Val Asn Arg Thr His Gln<br>        35                     40                      45 | | 144 |
| tac tca gaa aag gga aga tgg aca aca aac acc gaa act gga gca ccg<br>Tyr Ser Glu Lys Gly Arg Trp Thr Thr Asn Thr Glu Thr Gly Ala Pro<br>50                      55                     60 | | 192 |
| caa ctc aac ccg att gat ggg cca ctg cca gaa gac aat gaa cca agt<br>Gln Leu Asn Pro Ile Asp Gly Pro Leu Pro Glu Asp Asn Glu Pro Ser<br>65                      70                     75                     80 | | 240 |
| ggt tat gcc caa aca gat tgt gta ttg gag gcg atg gct ttc ctt gag<br>Gly Tyr Ala Gln Thr Asp Cys Val Leu Glu Ala Met Ala Phe Leu Glu<br>                       85                     90                       95 | | 288 |
| gaa tcc cat cct ggt att ttt gaa aac tcg tgt att gaa acg atg gag<br>Glu Ser His Pro Gly Ile Phe Glu Asn Ser Cys Ile Glu Thr Met Glu<br>                 100                    105                 110 | | 336 |
| gtt gtt cag caa aca cga gta gac aag ctg aca caa ggc cga cag acc<br>Val Val Gln Gln Thr Arg Val Asp Lys Leu Thr Gln Gly Arg Gln Thr<br>             115                    120                 125 | | 384 |
| tat gac tgg act cta aat aga aac caa cct gct gca aca gca ttg gcc<br>Tyr Asp Trp Thr Leu Asn Arg Asn Gln Pro Ala Ala Thr Ala Leu Ala<br>130                     135                    140 | | 432 |
| aac aca ata gaa gtg ttc aga tca aat ggc ctc acg gcc aat gag tct<br>Asn Thr Ile Glu Val Phe Arg Ser Asn Gly Leu Thr Ala Asn Glu Ser<br>145                     150                    155                 160 | | 480 |
| gga agg ctc ata gac ttc ctt aag gat gta atg gag tca atg aac aaa<br>Gly Arg Leu Ile Asp Phe Leu Lys Asp Val Met Glu Ser Met Asn Lys<br>                     165                    170                 175 | | 528 |
| gaa gaa atg ggg atc aca act cat ttt cag aga aag aga cgg gtg aga<br>Glu Glu Met Gly Ile Thr Thr His Phe Gln Arg Lys Arg Arg Val Arg<br>                 180                    185                 190 | | 576 |
| gac aat atg act aag aaa atg ata aca cag aga aca atg ggt aaa aag<br>Asp Asn Met Thr Lys Lys Met Ile Thr Gln Arg Thr Met Gly Lys Lys<br>             195                    200                 205 | | 624 |
| aag cag aga ttg aac aaa agg agt tat cta att aga gca ttg acc ctg<br>Lys Gln Arg Leu Asn Lys Arg Ser Tyr Leu Ile Arg Ala Leu Thr Leu<br>210                     215                    220 | | 672 |
| aac aca atg acc aaa gat gct gag aga ggg aag cta aaa cgg aga gca<br>Asn Thr Met Thr Lys Asp Ala Glu Arg Gly Lys Leu Lys Arg Arg Ala<br>225                     230                    235                 240 | | 720 |
| att gca acc cca ggg atg caa ata agg ggg ttt gta tac ttt gtt gag<br>Ile Ala Thr Pro Gly Met Gln Ile Arg Gly Phe Val Tyr Phe Val Glu<br>                     245                    250                 255 | | 768 |
| aca ctg gca agg agt ata tgt gag aaa ctt gaa caa tca ggg ttg cca<br>Thr Leu Ala Arg Ser Ile Cys Glu Lys Leu Glu Gln Ser Gly Leu Pro<br>             260                    265                 270 | | 816 |
| gtt gga ggc aat gag aag aaa gca aag ttg gca aat gtt gta agg aag<br>Val Gly Gly Asn Glu Lys Lys Ala Lys Leu Ala Asn Val Val Arg Lys<br>                 275                    280                 285 | | 864 |
| atg atg acc aat tct cag gac acc gaa ctt tct ttc acc atc act gga<br>Met Met Thr Asn Ser Gln Asp Thr Glu Leu Ser Phe Thr Ile Thr Gly<br>290                     295                    300 | | 912 |
| gat aac acc aaa tgg aac gaa aat cag aat cct cgg atg ttt ttg gcc<br>Asp Asn Thr Lys Trp Asn Glu Asn Gln Asn Pro Arg Met Phe Leu Ala<br>305                     310                    315                 320 | | 960 |
| atg atc aca tat atg acc aga aat cag ccc gaa tgg ttc aga aat gtt<br>Met Ile Thr Tyr Met Thr Arg Asn Gln Pro Glu Trp Phe Arg Asn Val<br>                     325                    330                 335 | | 1008 |

```
cta agt att gct cca ata atg ttc tca aac aaa atg gcg aga ctg gga      1056
Leu Ser Ile Ala Pro Ile Met Phe Ser Asn Lys Met Ala Arg Leu Gly
        340                 345                 350 aaa ggg tat atg ttt gag agc aag agt atg aaa ctt aga act caa ata      1104
Lys Gly Tyr Met Phe Glu Ser Lys Ser Met Lys Leu Arg Thr Gln Ile
    355                 360                 365 cct gca gaa atg cta gca agc atc gat ttg aaa tat ttc aat gat tca      1152
Pro Ala Glu Met Leu Ala Ser Ile Asp Leu Lys Tyr Phe Asn Asp Ser
370                 375                 380 aca aga aag aag att gaa aaa atc cga tcg ctc tta ata gag ggg act      1200
Thr Arg Lys Lys Ile Glu Lys Ile Arg Ser Leu Leu Ile Glu Gly Thr
385                 390                 395                 400 gca tca ttg agc cct gga atg atg atg ggc atg ttc aat atg tta agc      1248
Ala Ser Leu Ser Pro Gly Met Met Met Gly Met Phe Asn Met Leu Ser
                405                 410                 415 act gta tta ggc gtc tcc atc ctg aat ctt gga caa aag aga tac acc      1296
Thr Val Leu Gly Val Ser Ile Leu Asn Leu Gly Gln Lys Arg Tyr Thr
            420                 425                 430 aag act act tac tgg tgg gat ggt ctt caa tcc tct gac gat ttt gct      1344
Lys Thr Thr Tyr Trp Trp Asp Gly Leu Gln Ser Ser Asp Asp Phe Ala
        435                 440                 445 ctg att gtg aat gca ccc aat cat gaa ggg att caa gcc gga gtc gac      1392
Leu Ile Val Asn Ala Pro Asn His Glu Gly Ile Gln Ala Gly Val Asp
450                 455                 460 agg ttt tat cga acc tgt aag cta ctt gga atc aat atg agc aag aaa      1440
Arg Phe Tyr Arg Thr Cys Lys Leu Leu Gly Ile Asn Met Ser Lys Lys
465                 470                 475                 480 aag tct tac ata aac aga aca ggt aca ttt gaa ttc aca agt ttt ttc      1488
Lys Ser Tyr Ile Asn Arg Thr Gly Thr Phe Glu Phe Thr Ser Phe Phe
                485                 490                 495 tat cgt tat ggg ttt gtt gcc aat ttc agc atg gag ctt ccc agt ttt      1536
Tyr Arg Tyr Gly Phe Val Ala Asn Phe Ser Met Glu Leu Pro Ser Phe
            500                 505                 510 ggg gtg tct ggg atc aac gag tca gcg gac atg agt att gga gtt act      1584
Gly Val Ser Gly Ile Asn Glu Ser Ala Asp Met Ser Ile Gly Val Thr
        515                 520                 525 gtc atc aaa aac aat atg ata aac aat gat ctt ggt cca gca aca gct      1632
Val Ile Lys Asn Asn Met Ile Asn Asn Asp Leu Gly Pro Ala Thr Ala
530                 535                 540 caa atg gcc ctt cag ttg ttc atc aaa gat tac agg tac acg tac cga      1680
Gln Met Ala Leu Gln Leu Phe Ile Lys Asp Tyr Arg Tyr Thr Tyr Arg
545                 550                 555                 560 tgc cat aga ggt gac aca caa ata caa acc cga aga tca ttt gaa ata      1728
Cys His Arg Gly Asp Thr Gln Ile Gln Thr Arg Arg Ser Phe Glu Ile
                565                 570                 575 aag aaa ctg tgg gag caa acc cgt tcc aaa gct gga ctg ctg gtc tcc      1776
Lys Lys Leu Trp Glu Gln Thr Arg Ser Lys Ala Gly Leu Leu Val Ser
            580                 585                 590 gac gga ggc cca aat tta tac aac att aga aat ctc cac att cct gaa      1824
Asp Gly Gly Pro Asn Leu Tyr Asn Ile Arg Asn Leu His Ile Pro Glu
        595                 600                 605 gtc tgc cta aaa tgg gaa ttg atg gat gag gat tac cag ggg cgt tta      1872
Val Cys Leu Lys Trp Glu Leu Met Asp Glu Asp Tyr Gln Gly Arg Leu
610                 615                 620 tgc aac cca ctg aac cca ttt gtc agc cat aaa gaa att gaa tca atg      1920
Cys Asn Pro Leu Asn Pro Phe Val Ser His Lys Glu Ile Glu Ser Met
625                 630                 635                 640 aac aat gca gtg atg atg cca gca cat ggt cca gcc aaa aac atg gag      1968
Asn Asn Ala Val Met Met Pro Ala His Gly Pro Ala Lys Asn Met Glu
                645                 650                 655
```

-continued

```
tat gat gct gtt gca aca aca cac tcc tgg atc ccc aaa aga aat cga    2016
Tyr Asp Ala Val Ala Thr Thr His Ser Trp Ile Pro Lys Arg Asn Arg
        660                 665                 670 tcc atc ttg aat aca agt caa aga gga gta ctt gag gat gaa caa atg    2064
Ser Ile Leu Asn Thr Ser Gln Arg Gly Val Leu Glu Asp Glu Gln Met
            675                 680                 685 tac caa agg tgc tgc aat tta ttt gaa aaa ttc ttc ccc agc agt tca    2112
Tyr Gln Arg Cys Cys Asn Leu Phe Glu Lys Phe Phe Pro Ser Ser Ser
690                 695                 700 tac aga aga cca gtc ggg ata tcc agt atg gtg gag gct atg gtt tcc    2160
Tyr Arg Arg Pro Val Gly Ile Ser Ser Met Val Glu Ala Met Val Ser
705                 710                 715                 720 aga gcc cga att gat gca cgg att gat ttc gaa tct gga agg ata aag    2208
Arg Ala Arg Ile Asp Ala Arg Ile Asp Phe Glu Ser Gly Arg Ile Lys
                725                 730                 735 aaa gaa gag ttc act gag atc atg aag atc tgt tcc acc att gaa gag    2256
Lys Glu Glu Phe Thr Glu Ile Met Lys Ile Cys Ser Thr Ile Glu Glu
            740                 745                 750 ctc aga cgg caa aaa tag                                              2274
Leu Arg Arg Gln Lys
        755
```

<210> SEQ ID NO 4
<211> LENGTH: 757
<212> TYPE: PRT
<213> ORGANISM: Influenza A Virus

<400> SEQUENCE: 4

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Met Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
```

```
                225                 230                 235                 240
Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
            290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                    325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
                355                 360                 365

Pro Ala Glu Met Leu Ala Ser Ile Asp Leu Lys Tyr Phe Asn Asp Ser
            370                 375                 380

Thr Arg Lys Lys Ile Glu Lys Ile Arg Ser Leu Leu Ile Glu Gly Thr
385                 390                 395                 400

Ala Ser Leu Ser Pro Gly Met Met Met Gly Met Phe Asn Met Leu Ser
                    405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Ile Gln Ala Gly Val Asp
            450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                    485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                    565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                    645                 650                 655
```

```
Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
        740                 745                 750

Leu Arg Arg Gln Lys
        755

<210> SEQ ID NO 5
<211> LENGTH: 1437
<212> TYPE: DNA
<213> ORGANISM: Influenza A Virus
<220> FEATURE:
<221> NAME/KEY: CDS
<222> LOCATION: (1)..(1437)
<223> OTHER INFORMATION: PA of Influenza A/Puerto Rico/8/1934 H1N1

<400> SEQUENCE: 5 aac ggc tac att gag ggc aag ctg tct caa atg tcc aaa gaa gta aat    48
Asn Gly Tyr Ile Glu Gly Lys Leu Ser Gln Met Ser Lys Glu Val Asn
1               5                   10                  15 gct aga att gaa cct ttt ttg aaa aca aca cca aga cca ctt aga ctt    96
Ala Arg Ile Glu Pro Phe Leu Lys Thr Thr Pro Arg Pro Leu Arg Leu
                20                  25                  30 ccg aat ggg cct ccc tgt tct cag cgg tcc aaa ttc ctg ctg atg gat   144
Pro Asn Gly Pro Pro Cys Ser Gln Arg Ser Lys Phe Leu Leu Met Asp
            35                  40                  45 gcc tta aaa tta tgc att gag gac cca agt cat gaa gga gag gga ata   192
Ala Leu Lys Leu Cys Ile Glu Asp Pro Ser His Glu Gly Glu Gly Ile
        50                  55                  60 ccg cta tat gat gca atc aaa tgc atg aga aca ttc ttt gga tgg aag   240
Pro Leu Tyr Asp Ala Ile Lys Cys Met Arg Thr Phe Phe Gly Trp Lys
65                  70                  75                  80 gaa ccc aat gtt gtt aaa cca cac gaa aag gga ata aat cca aat tat   288
Glu Pro Asn Val Val Lys Pro His Glu Lys Gly Ile Asn Pro Asn Tyr
                85                  90                  95 ctt ctg tca tgg aag caa gta ctg gca gaa ctg cag gac att gag aat   336
Leu Leu Ser Trp Lys Gln Val Leu Ala Glu Leu Gln Asp Ile Glu Asn
                100                 105                 110 gag gag aaa att cca aag act aaa aat atg aag aaa aca agt cag cta   384
Glu Glu Lys Ile Pro Lys Thr Lys Asn Met Lys Lys Thr Ser Gln Leu
        115                 120                 125 aag tgg gca ctt ggt gag aac atg gca cca gaa aag gta gac ttt gac   432
Lys Trp Ala Leu Gly Glu Asn Met Ala Pro Glu Lys Val Asp Phe Asp
130                 135                 140 gac tgt aaa gat gta ggt gat ttg aag caa tat gat agt gat gaa cca   480
Asp Cys Lys Asp Val Gly Asp Leu Lys Gln Tyr Asp Ser Asp Glu Pro
145                 150                 155                 160 gaa ttg agg tcg ctt gca agt tgg att cag aat gag ttt aac aag gca   528
Glu Leu Arg Ser Leu Ala Ser Trp Ile Gln Asn Glu Phe Asn Lys Ala
                165                 170                 175 tgc gaa ctg aca gat tca agc tgg ata gag ctc gat gag att gga gaa   576
Cys Glu Leu Thr Asp Ser Ser Trp Ile Glu Leu Asp Glu Ile Gly Glu
                180                 185                 190
```

```
gat gtg gct cca att gaa cac att gca agc atg aga agg aat tat ttc        624
Asp Val Ala Pro Ile Glu His Ile Ala Ser Met Arg Arg Asn Tyr Phe
        195                 200                 205 aca tca gag gtg tct cac tgc aga gcc aca gaa tac ata atg aag ggg        672
Thr Ser Glu Val Ser His Cys Arg Ala Thr Glu Tyr Ile Met Lys Gly
210                 215                 220 gtg tac atc aat act gcc ttg ctt aat gca tct tgt gca gca atg gat        720
Val Tyr Ile Asn Thr Ala Leu Leu Asn Ala Ser Cys Ala Ala Met Asp
225                 230                 235                 240 gat ttc caa tta att cca atg ata agc aag tgt aga act aag gag gga        768
Asp Phe Gln Leu Ile Pro Met Ile Ser Lys Cys Arg Thr Lys Glu Gly
        245                 250                 255 agg cga aag acc aac ttg tat ggt ttc atc ata aaa gga aga tcc cac        816
Arg Arg Lys Thr Asn Leu Tyr Gly Phe Ile Ile Lys Gly Arg Ser His
        260                 265                 270 tta agg aat gac acc gac gtg gta aac ttt gtg agc atg gag ttt tct        864
Leu Arg Asn Asp Thr Asp Val Val Asn Phe Val Ser Met Glu Phe Ser
        275                 280                 285 ctc act gac cca aga ctt gaa cca cat aaa tgg gag aag tac tgt gtt        912
Leu Thr Asp Pro Arg Leu Glu Pro His Lys Trp Glu Lys Tyr Cys Val
290                 295                 300 ctt gag ata gga gat atg ctt ata aga agt gcc ata ggc cag gtt tca        960
Leu Glu Ile Gly Asp Met Leu Ile Arg Ser Ala Ile Gly Gln Val Ser
305                 310                 315                 320 agg ccc atg ttc ttg tat gtg aga aca aat gga acc tca aaa att aaa       1008
Arg Pro Met Phe Leu Tyr Val Arg Thr Asn Gly Thr Ser Lys Ile Lys
        325                 330                 335 atg aaa tgg gga atg gag atg agg cgt tgc ctc ctc cag tca ctt caa       1056
Met Lys Trp Gly Met Glu Met Arg Arg Cys Leu Leu Gln Ser Leu Gln
        340                 345                 350 caa att gag agt atg att gaa gct gag tcc tct gtc aaa gag aaa gac       1104
Gln Ile Glu Ser Met Ile Glu Ala Glu Ser Ser Val Lys Glu Lys Asp
        355                 360                 365 atg acc aaa gag ttc ttt gag aac aaa tca gaa aca tgg ccc att gga       1152
Met Thr Lys Glu Phe Phe Glu Asn Lys Ser Glu Thr Trp Pro Ile Gly
370                 375                 380 gag tcc ccc aaa gga gtg gag gaa agt tcc att ggg aag gtc tgc agg       1200
Glu Ser Pro Lys Gly Val Glu Glu Ser Ser Ile Gly Lys Val Cys Arg
385                 390                 395                 400 act tta tta gca aag tcg gta ttc aac agc ttg tat gca tct cca caa       1248
Thr Leu Leu Ala Lys Ser Val Phe Asn Ser Leu Tyr Ala Ser Pro Gln
        405                 410                 415 cta gaa gga ttt tca gct gaa tca aga aaa ctg ctt ctt atc gtt cag       1296
Leu Glu Gly Phe Ser Ala Glu Ser Arg Lys Leu Leu Leu Ile Val Gln
        420                 425                 430 gct ctt agg gac aac ctg gaa cct ggg acc ttt gat ctt ggg ggg cta       1344
Ala Leu Arg Asp Asn Leu Glu Pro Gly Thr Phe Asp Leu Gly Gly Leu
        435                 440                 445 tat gaa gca att gag gag tgc ctg att aat gat ccc tgg gtt ttg ctt       1392
Tyr Glu Ala Ile Glu Glu Cys Leu Ile Asn Asp Pro Trp Val Leu Leu
        450                 455                 460 aat gct tct tgg ttc aac tcc ttc ctt aca cat gca ttg agt tag           1437
Asn Ala Ser Trp Phe Asn Ser Phe Leu Thr His Ala Leu Ser
465                 470                 475

<210> SEQ ID NO 6
<211> LENGTH: 478
<212> TYPE: PRT
<213> ORGANISM: Influenza A Virus

<400> SEQUENCE: 6
```

```
Asn Gly Tyr Ile Glu Gly Lys Leu Ser Gln Met Ser Lys Glu Val Asn
 1               5                  10                  15

Ala Arg Ile Glu Pro Phe Leu Lys Thr Thr Pro Arg Pro Leu Arg Leu
             20                  25                  30

Pro Asn Gly Pro Pro Cys Ser Gln Arg Ser Lys Phe Leu Leu Met Asp
         35                  40                  45

Ala Leu Lys Leu Cys Ile Glu Asp Pro Ser His Glu Gly Gly Ile
 50                  55                  60

Pro Leu Tyr Asp Ala Ile Lys Cys Met Arg Thr Phe Phe Gly Trp Lys
 65                  70                  75                  80

Glu Pro Asn Val Val Lys Pro His Glu Lys Gly Ile Asn Pro Asn Tyr
                 85                  90                  95

Leu Leu Ser Trp Lys Gln Val Leu Ala Glu Leu Gln Asp Ile Glu Asn
                100                 105                 110

Glu Glu Lys Ile Pro Lys Thr Lys Asn Met Lys Lys Thr Ser Gln Leu
            115                 120                 125

Lys Trp Ala Leu Gly Glu Asn Met Ala Pro Glu Lys Val Asp Phe Asp
130                 135                 140

Asp Cys Lys Asp Val Gly Asp Leu Lys Gln Tyr Asp Ser Asp Glu Pro
145                 150                 155                 160

Glu Leu Arg Ser Leu Ala Ser Trp Ile Gln Asn Glu Phe Asn Lys Ala
                165                 170                 175

Cys Glu Leu Thr Asp Ser Ser Trp Ile Glu Leu Asp Glu Ile Gly Glu
                180                 185                 190

Asp Val Ala Pro Ile Glu His Ile Ala Ser Met Arg Arg Asn Tyr Phe
            195                 200                 205

Thr Ser Glu Val Ser His Cys Arg Ala Thr Glu Tyr Ile Met Lys Gly
210                 215                 220

Val Tyr Ile Asn Thr Ala Leu Leu Asn Ala Ser Cys Ala Ala Met Asp
225                 230                 235                 240

Asp Phe Gln Leu Ile Pro Met Ile Ser Lys Cys Arg Thr Lys Glu Gly
                245                 250                 255

Arg Arg Lys Thr Asn Leu Tyr Gly Phe Ile Ile Lys Gly Arg Ser His
                260                 265                 270

Leu Arg Asn Asp Thr Asp Val Val Asn Phe Val Ser Met Glu Phe Ser
            275                 280                 285

Leu Thr Asp Pro Arg Leu Glu Pro His Lys Trp Glu Lys Tyr Cys Val
290                 295                 300

Leu Glu Ile Gly Asp Met Leu Ile Arg Ser Ala Ile Gly Gln Val Ser
305                 310                 315                 320

Arg Pro Met Phe Leu Tyr Val Arg Thr Asn Gly Thr Ser Lys Ile Lys
                325                 330                 335

Met Lys Trp Gly Met Glu Met Arg Arg Cys Leu Leu Gln Ser Leu Gln
                340                 345                 350

Gln Ile Glu Ser Met Ile Glu Ala Glu Ser Ser Val Lys Glu Lys Asp
            355                 360                 365

Met Thr Lys Glu Phe Phe Glu Asn Lys Ser Glu Thr Trp Pro Ile Gly
370                 375                 380

Glu Ser Pro Lys Gly Val Glu Ser Ser Ile Gly Lys Val Cys Arg
385                 390                 395                 400

Thr Leu Leu Ala Lys Ser Val Phe Asn Ser Leu Tyr Ala Ser Pro Gln
                405                 410                 415

Leu Glu Gly Phe Ser Ala Glu Ser Arg Lys Leu Leu Leu Ile Val Gln
```

```
                       420                 425                 430
Ala Leu Arg Asp Asn Leu Glu Pro Gly Thr Phe Asp Leu Gly Gly Leu
            435                 440                 445

Tyr Glu Ala Ile Glu Glu Cys Leu Ile Asn Asp Pro Trp Val Leu Leu
        450                 455                 460

Asn Ala Ser Trp Phe Asn Ser Phe Leu Thr His Ala Leu Ser
465                 470                 475

<210> SEQ ID NO 7
<211> LENGTH: 243
<212> TYPE: DNA
<213> ORGANISM: Influenza A Virus
<220> FEATURE:
<221> NAME/KEY: CDS
<222> LOCATION: (1)..(243)
<223> OTHER INFORMATION: PB1 of Influenza A/Puerto Rico/8/1934 H1N1

<400> SEQUENCE: 7 atg gat gtc aat ccg acc tta ctt ttc tta aaa gtg cca gca caa aat       48
Met Asp Val Asn Pro Thr Leu Leu Phe Leu Lys Val Pro Ala Gln Asn
1               5                   10                  15 gct ata agc aca act ttc cct tat act gga gac

H5N1

<400> SEQUENCE: 9

```
aac ggc tgc att gag ggc aag ctt tct caa at

```
ctc gag ata gga gac atg ctc cta cgg act gca gta ggc caa gtt tca       960
Leu Glu Ile Gly Asp Met Leu Leu Arg Thr Ala Val Gly Gln Val Ser
305                 310                 315                 320 agg ccc atg ttc ctg tat gtg aga acc aat gga acc tcc aag atc aaa      1008
Arg Pro Met Phe Leu Tyr Val Arg Thr Asn Gly Thr Ser Lys Ile Lys
                325                 330                 335 atg aaa tgg ggc atg gaa atg agg cga tgc ctt ctt caa tcc ctt caa      1056
Met Lys Trp Gly Met Glu Met Arg Arg Cys Leu Leu Gln Ser Leu Gln
            340                 345                 350 caa att gaa agc atg att gaa gcc gag tct tct gtc aaa gag aag gac      1104
Gln Ile Glu Ser Met Ile Glu Ala Glu Ser Ser Val Lys Glu Lys Asp
        355                 360                 365 atg acc aaa gaa ttc ttt gaa aac aaa tca gag aca tgg ccg att gga      1152
Met Thr Lys Glu Phe Phe Glu Asn Lys Ser Glu Thr Trp Pro Ile Gly
370                 375                 380 gag tcc ccc aaa gga gtg gag gaa gga tcc atc gga aag gtg tgc aga      1200
Glu Ser Pro Lys Gly Val Glu Glu Gly Ser Ile Gly Lys Val Cys Arg
385                 390                 395                 400 acc ttg ctg gcg aag tct gtg ttc aac agt tta tat gca tct cca caa      1248
Thr Leu Leu Ala Lys Ser Val Phe Asn Ser Leu Tyr Ala Ser Pro Gln
                405                 410                 415 ctc gag ggg ttt tca gct gaa tca aga aaa ttg ctt ctc att gct cag      1296
Leu Glu Gly Phe Ser Ala Glu Ser Arg Lys Leu Leu Leu Ile Ala Gln
            420                 425                 430 gca ctt agg gac aac ctg gaa cct ggg acc ttc gat ctt gga ggg cta      1344
Ala Leu Arg Asp Asn Leu Glu Pro Gly Thr Phe Asp Leu Gly Gly Leu
        435                 440                 445 tat gaa gca att gag gag tgc ctg att aac gat ccc tgg gtt ttg ctt      1392
Tyr Glu Ala Ile Glu Glu Cys Leu Ile Asn Asp Pro Trp Val Leu Leu
450                 455                 460 aat gcg tct tgg ttc aac tcc ttc ctc aca cat gca ctg aaa               1434
Asn Ala Ser Trp Phe Asn Ser Phe Leu Thr His Ala Leu Lys
465                 470                 475
```

<210> SEQ ID NO 10
<211> LENGTH: 478
<212> TYPE: PRT
<213> ORGANISM: Influenza A Virus

<400> SEQUENCE: 10

```
Asn Gly Cys Ile Glu Gly Lys Leu Ser Gln Met Ser Lys Glu Val Asn
1               5                   10                  15

Ala Arg Ile Glu Pro Phe Leu Lys Thr Thr Pro Arg Pro Leu Arg Leu
            20                  25                  30

Pro Asp Gly Pro Pro Cys Ser Gln Arg Ser Lys Phe Leu Leu Met Asp
        35                  40                  45

Ala Leu Lys Leu Asn Ile Glu Asp Pro Ser His Glu Gly Glu Gly Ile
    50                  55                  60

Pro Leu Tyr Asp Ala Ile Lys Cys Met Lys Thr Phe Phe Gly Trp Lys
65                  70                  75                  80

Glu Pro Asn Ile Val Lys Pro His Glu Lys Gly Ile Asn Pro Asn Tyr
                85                  90                  95

Leu Leu Ala Trp Lys Gln Val Leu Ala Glu Leu Gln Asp Ile Glu Asn
            100                 105                 110

Glu Glu Lys Ile Pro Lys Thr Lys Asn Met Lys Lys Thr Gly Gln Leu
        115                 120                 125

Lys Trp Ala Leu Gly Glu Asn Met Ala Pro Glu Lys Val Asp Phe Glu
    130                 135                 140

Asp Cys Lys Asp Val Ser Asp Leu Arg Gln Tyr Asp Ser Asp Glu Pro
```

```
                145                 150                 155                 160
Glu Ser Arg Ser Leu Ala Ser Trp Ile Gln Ser Glu Phe Asn Lys Ala
                    165                 170                 175
Cys Glu Leu Thr Asp Ser Ser Trp Ile Glu Leu Asp Glu Ile Gly Glu
                    180                 185                 190
Asp Val Ala Pro Ile Glu His Ile Ala Ser Met Arg Arg Asn Tyr Phe
                    195                 200                 205
Thr Ala Glu Val Ser His Cys Arg Ala Thr Glu Tyr Ile Met Lys Gly
                    210                 215                 220
Val Tyr Ile Asn Thr Ala Leu Leu Asn Ala Ser Cys Ala Ala Met Asp
225                 230                 235                 240
Asp Phe Gln Leu Ile Pro Met Ile Ser Lys Cys Arg Thr Lys Glu Gly
                    245                 250                 255
Arg Arg Lys Thr Asn Leu Tyr Gly Phe Ile Ile Lys Gly Arg Ser His
                    260                 265                 270
Leu Arg Asn Asp Thr Asp Val Val Asn Phe Val Ser Met Glu Phe Ser
                    275                 280                 285
Leu Thr Asp Pro Arg Leu Glu Pro His Lys Trp Glu Lys Tyr Cys Val
                    290                 295                 300
Leu Glu Ile Gly Asp Met Leu Leu Arg Thr Ala Val Gly Gln Val Ser
305                 310                 315                 320
Arg Pro Met Phe Leu Tyr Val Arg Thr Asn Gly Thr Ser Lys Ile Lys
                    325                 330                 335
Met Lys Trp Gly Met Glu Met Arg Arg Cys Leu Leu Gln Ser Leu Gln
                    340                 345                 350
Gln Ile Glu Ser Met Ile Glu Ala Glu Ser Ser Val Lys Glu Lys Asp
                    355                 360                 365
Met Thr Lys Glu Phe Phe Glu Asn Lys Ser Glu Thr Trp Pro Ile Gly
                    370                 375                 380
Glu Ser Pro Lys Gly Val Glu Glu Gly Ser Ile Gly Lys Val Cys Arg
385                 390                 395                 400
Thr Leu Leu Ala Lys Ser Val Phe Asn Ser Leu Tyr Ala Ser Pro Gln
                    405                 410                 415
Leu Glu Gly Phe Ser Ala Glu Ser Arg Lys Leu Leu Leu Ile Ala Gln
                    420                 425                 430
Ala Leu Arg Asp Asn Leu Glu Pro Gly Thr Phe Asp Leu Gly Gly Leu
                    435                 440                 445
Tyr Glu Ala Ile Glu Glu Cys Leu Ile Asn Asp Pro Trp Val Leu Leu
                    450                 455                 460
Asn Ala Ser Trp Phe Asn Ser Phe Leu Thr His Ala Leu Lys
465                 470                 475

<210> SEQ ID NO 11
<211> LENGTH: 243
<212> TYPE: DNA
<213> ORGANISM: Influenza A Virus
<220> FEATURE:
<221> NAME/KEY: CDS
<222> LOCATION: (1)..(243)
<223> OTHER INFORMATION: PB1 of Influenza A/Duck/Hong Kong/2986.1/2000
      H5N1

<400> SEQUENCE: 11 atg gat gtc aat ccg act tta ctt ttc tta aaa gtg cca gcg caa aat    48
Met Asp Val Asn Pro Thr Leu Leu Phe Leu Lys Val Pro Ala Gln Asn
1               5                   10                  15 gct ata agt acc aca ttc cct tat act gga gat cct cca tac agc cat    96
```

```
Ala Ile Ser Thr Thr Phe Pro Tyr Thr Gly Asp Pro Tyr Ser His
            20              25              30 gga aca gga aca gga tac acc atg gac aca gtc aac aga aca cat caa    144
Gly Thr Gly Thr Gly Tyr Thr Met Asp Thr Val Asn Arg Thr His Gln
        35              40              45 tat tca gaa cag ggg aaa tgg aca acg aac aca gag act gga gca ccc    192
Tyr Ser Glu Gln Gly Lys Trp Thr Thr Asn Thr Glu Thr Gly Ala Pro
    50              55              60 caa ctc aat ccg att gat gga cca ctg cct gag gat aat gag ccg agt    240
Gln Leu Asn Pro Ile Asp Gly Pro Leu Pro Glu Asp Asn Glu Pro Ser
65              70              75              80 ggg                                                                 243
Gly

<210> SEQ ID NO 12
<211> LENGTH: 81
<212> TYPE: PRT
<213> ORGANISM: Influenza A Virus

<400> SEQUENCE: 12

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Tyr Ser His
            20              25              30

Gly Thr Gly Thr Gly Tyr Thr Met Asp Thr Val Asn Arg Thr His Gln
        35              40              45

Tyr Ser Glu Gln Gly Lys Trp Thr Thr Asn Thr Glu Thr Gly Ala Pro
    50              55              60

Gln Leu Asn Pro Ile Asp Gly Pro Leu Pro Glu Asp Asn Glu Pro Ser
65              70              75              80

Gly

<210> SEQ ID NO 13
<211> LENGTH: 6
<212> TYPE: PRT
<213> ORGANISM: Influenza A Virus
<220> FEATURE:
<221> NAME/KEY: Amino Acids
<222> LOCATION: (1)..(6)
<223> OTHER INFORMATION: PTLLFL included in PB1 of Influenza A/Puerto
      Rico/8/1934 H1N1

<400> SEQUENCE: 13

Pro Thr Leu Leu Phe Leu
1               5
```